(12) United States Patent
Irdam

(10) Patent No.: US 11,453,641 B2
(45) Date of Patent: *Sep. 27, 2022

(54) METHODS OF TREATING NEUROFIBROMATOSIS WITH N-((R)-2,3-DIHYDROXYPROPOXY)-3,4-DIFLUORO-2-(2-FLUORO-4-IODOPHENYLAMINO)-BENZAMIDE

(71) Applicant: Warner-Lambert Company LLC, New York, NY (US)

(72) Inventor: Erwin Irdam, Melrose, MA (US)

(73) Assignee: Warner-Lambert Company LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/357,593

(22) Filed: Jun. 24, 2021

(65) Prior Publication Data

US 2022/0259142 A1     Aug. 18, 2022

Related U.S. Application Data

(63) Continuation of application No. 17/178,022, filed on Feb. 17, 2021, now Pat. No. 11,066,358.

(51) Int. Cl.
| | |
|---|---|
| *A61K 31/16* | (2006.01) |
| *A61P 35/00* | (2006.01) |
| *C07C 237/28* | (2006.01) |
| *A61K 9/48* | (2006.01) |
| *A61K 9/20* | (2006.01) |
| *A61K 9/00* | (2006.01) |

(52) U.S. Cl.
CPC .......... *C07C 237/28* (2013.01); *A61K 9/0053* (2013.01); *A61K 9/20* (2013.01); *A61K 9/48* (2013.01); *C07B 2200/13* (2013.01)

(58) Field of Classification Search
CPC ................................ A61K 31/16; A61P 35/00
USPC ....................................................... 514/622
See application file for complete search history.

(56) References Cited

U.S. PATENT DOCUMENTS

| | | | |
|---|---|---|---|
| 4,965,270 A | 10/1990 | Harden et al. | |
| 6,960,614 B2 | 11/2005 | Barrett et al. | |
| 7,060,856 B2 | 6/2006 | Macikenas et al. | |
| 7,411,001 B2 | 8/2008 | Barrett et al. | |
| 11,066,358 B1 * | 7/2021 | Irdam | C07C 237/28 |
| 11,084,780 B1 * | 8/2021 | Patterson | A61K 9/4825 |

FOREIGN PATENT DOCUMENTS

| | | |
|---|---|---|
| WO | WO-2002006213 A2 | 1/2002 |
| WO | WO-2004045617 A1 | 6/2004 |
| WO | WO-2005040098 A1 | 5/2005 |
| WO | WO-2006061712 A2 | 6/2006 |
| WO | WO-2006134469 A1 | 12/2006 |
| WO | WO-2007042885 A2 | 4/2007 |

OTHER PUBLICATIONS

Abiko, A. and Masamune, S., "Synthesis of (+)-Siphonarienone: Asymmetric Alkylation using a Chiral Benzopyrano-isoxazolidine Auxiliary," *Tetrahedron Letters* 37(7):1081-1084, Elsevier Science Ltd., Netherlands (1996).

Komiotis, D., et al., "Synthesis of dl-cis- and (4R,5R)-trans-7-(2,2-Dimethyl-4-(phenylsulfonyl)aminomethyl-1,3-dioxolan-5-yl)-5(Z)-heptenoic Acid Analogues as Platelet Thromboxane A2 Receptor Antagonists," *Eur. J. Med. Chem.* 30(4):321-326, Elsevier, Netherlands (1995).

NCT00147550, "A Multicenter, Open-Label, Noncomparative Phase 1-2 Clinical and Pharmacokinetic Study of Oral PD 0325901 In Patients With Advanced Cancer," sponsored by Pfizer, first posted Sep. 7, 2005, accessed at https://clinicaltrials.gov/ct2/show/record/NCT00147550 on Feb. 22, 2021, 3 pages.

NCT00174369, "Phase 2 Study of the MEK Inhibitor PD-0325901 In Patients With Advanced Non-Small Cell Lung Cancer," sponsored by Pfizer, first posted Sep. 15, 2005, accessed at https://clinicaltrials.gov/ct2/show/record/NCT00174369 on Feb. 22, 2021, 3 pages.

NCT01347866, "A Multi-arm Phase 1 Dose Escalation Study of the Safety, Pharmacokinetics, and Pharmacodynamics of the Dual Pi3k/Mtor Inhibitors Pf-04691502 and Pf-05212384 In Combination With Experimental or Approved Anticancer Agents in Patients With Advanced Cancer," sponsored by Pfizer, first posted May 4, 2011, accessed at https://clinicaltrials.gov/ct2/show/record/NCT01347866 on Feb. 22, 2021, 6 pages.

NCT02022982, "Phase I/II Study of the CDK4/6 Inhibitor Palbociclib (PD-0332991) in Combination With the MEK Inhibitor PD-0325901 for Patients With KRAS Mutant Non-Small Cell Lung Cancer and Other Solid Tumors," sponsored by Dana-Farber Cancer Institute, first posted Dec. 30, 2013, accessed at https://clinicaltrials.gov/ct2/show/record/NCT02022982 on Feb. 22, 2021, 4 pages.

NCT02039336, "Phase I/II Study With the Combination of Dacomitinib and PD-0325901 in Metastatic KRAS Mutation Positive Non-small Cell Lung Cancer," sponsered by The Netherlands Cancer Institute, first posted Jan. 17, 2014, accessed at https://clinicaltrials.gov/ct2/show/record/NCT02039336 on Feb. 22, 2021, 3 pages.

(Continued)

*Primary Examiner* — Raymond J Henley, III
(74) *Attorney, Agent, or Firm* — Sterne, Kessler, Goldstein & Fox P.L.L.C.

(57) ABSTRACT

The present disclosure relates to: a) a crystalline composition of essentially pure Form IV of N-((R)-2,3-dihydroxypropoxy)-3,4-difluoro-2-(2-fluoro-4-iodo-phenylamino)-benzamide; b) pharmaceutical compositions comprising the crystalline composition of essentially pure Form IV of N-((R)-2,3-dihydroxypropoxy)-3,4-difluoro-2-(2-fluoro-4-iodo-phenylamino)-benzamide, and, optionally, a pharmaceutically acceptable carrier; and c) methods of treating a tumor, a cancer, or a Rasopathy disorder by administering the crystalline composition of essentially pure Form IV of N-((R)-2,3-dihydroxypropoxy)-3,4-difluoro-2-(2-fluoro-4-iodo-phenylamino)-benzamide to a subject in need thereof.

6 Claims, 4 Drawing Sheets

(56) References Cited

OTHER PUBLICATIONS

NCT02096471, "A Phase 2 Trial of the MEK Inhibitor PD-0325901 in Adolescents and Adults with NF1-Associated Morbid Plexiform Neurofibromas," sponsored by University of Alabama at Birmingham, first posted Mar. 26, 2014, accessed at https://clinicaltrials.gov/ct2/show/NCT02096471 on Feb. 22, 2021, 6 pages.

NCT02510001, "A Sequential Phase I Study of MEK1/2 Inhibitors PD-0325901 or Binimetinib Combined with cMET Inhibitor PF-02341066 in Patients With RAS Mutant and RAS Wild Type (With Aberrant c-MET) Colorectal Cancer," sponsored by University of Oxford, first posted Jul. 28, 2015, accessed at https://clinicaltrials.gov/ct2/show/record/NCT02510001 on Feb. 22, 2021, 11 pages.

NCT03170206, "Phase I/II Study of the CDK4/6 Inhibitor Palbociclib (PD-0332991) in Combination With the MEK Inhibitor Binimetinib (MEK162) for Patients With Advanced KRAS Mutant Non-Small Cell Lung Cancer," sponsored by Dana-Farber Cancer Institute, first posted May 30, 2017, accessed at https://clinicaltrials.gov/ct2/show/record/NCT03170206 on Feb. 22, 2021, 5 pages.

NCT03905148, "A Phase 1b, Open-Label, Dose-escalation and Expansion Study to Investigate the Safety, Pharmacokinetics and Antitumor Activities of a RAF Dimer Inhibitor BGB-283 in Combination With MEK Inhibitor PD-0325901 in Patients With Advanced or Refractory Solid Tumors," sponsored by BeiGene, first posted Apr. 5, 2019, accessed at https://clinicaltrials.gov/ct2/show/record/NCT03905148 on Feb. 22, 2021, 4 pages.

NCT03962543, "A Phase 2b Trial of the MEK 1/2 Inhibitor (MEKi) PD-0325901 in Adult and Pediatric Patients With Neurofibromatosis Type 1 (NF1)-Associated Inoperable Plexiform Neurofibromas (PNs) That Are Causing Significant Morbidity," sponsored by SpringWorks Therapeutics, Inc., first posted May 24, 2019, accessed at https://clinicaltrials.gov/ct2/show/NCT03962543 on Feb. 22, 2021, 4 pages.

The United States Pharmacopeia—National Formulary (NF18), "<941> X-Ray Diffraction," $23^{rd}$ Edition, pp. 1843-1844 (1995).

Co-pending Application, U.S. Appl. No. 17/177,966, inventors Patterson, K., et al., filed Feb. 17, 2021 (Not Yet Published).

Co-pending Application, U.S. Appl. No. 17/177,999, inventors Patterson, K., et al., filed Feb. 17, 2021 (Not Yet Published).

Florence, A. J., "Polymorph screening in pharmaceutical development," European Pharmaceutical Review, Issue 4, accessed at URL: [https://www.europeanpharmaceuticalreview.com/article/3659/polymorph-screening-in-pharmaceutical-development/] on Mar. 7, 2018, 14 pages (Aug. 19, 2010).

International Search Report and Written Opinion for International Application No. PCT/US2021/018373, European Patent Office, Netherlands, dated Dec. 8, 2021, 20 pages.

International Search Report and Written Opinion for International Application No. PCT/US2021/018378, European Patent Office, Netherlands, dated Nov. 12, 2021, 14 pages.

International Search Report and Written Opinion for International Application No. PCT/US2021/018381, European Patent Office, Netherlands, dated Dec. 8, 2021, 25 pages.

* cited by examiner

METHODS OF TREATING NEUROFIBROMATOSIS WITH N-((R)-2,3-DIHYDROXYPROPOXY)-3,4-DIFLUORO-2-(2-FLUORO-4-IODOPHENYLAMINO)-BENZAMIDE

CROSS-REFERENCE TO RELATED APPLICATION

This application is a continuation of U.S. application Ser. No. 17/178,022, now U.S. Pat. No. 11,066,358, filed Feb. 17, 2021, which is incorporated by reference in its entirety herein.

FIELD OF THE INVENTION

The present disclosure relates to: a) a crystalline composition that is essentially pure Form IV of N-((R)-2,3-dihydroxypropoxy)-3,4-difluoro-2-(2-fluoro-4-iodo-phenylamino)-benzamide; b) pharmaceutical compositions comprising the crystalline composition that is essentially pure Form IV of N-((R)-2,3-dihydroxypropoxy)-3,4-difluoro-2-(2-fluoro-4-iodo-phenylamino)-benzamide, and, optionally, a pharmaceutically acceptable carrier; and c) methods of treating a tumor, a cancer, or a Rasopathy disorder by administering the crystalline composition that is essentially pure Form IV of N-((R)-2,3-dihydroxypropoxy)-3,4-difluoro-2-(2-fluoro-4-iodo-phenylamino)-benzamide to a subject in need thereof.

BACKGROUND

N-((R)-2,3-dihydroxypropoxy)-3,4-difluoro-2-(2-fluoro-4-iodo-phenylamino)-benzamide ("mirdametinib", or "PD-0325901") is a small molecule drug which has been designed to inhibit mitogen-activated protein kinase kinase 1 ("MEK1") and mitogen-activated protein kinase kinase 2 ("MEK2"). MEK1 and MEK2 are proteins that play key roles in the mitogen-activated protein kinase ("MAPK") signaling pathway. The MAPK pathway is critical for cell survival and proliferation, and overactivation of this pathway has been shown to lead to tumor development and growth. Mirdametinib is a highly potent and specific allosteric non-ATP-competitive inhibitor of MEK1 and MEK2. By virtue of its mechanism of action, mirdametinib leads to significantly inhibited phosphorylation of the extracellular regulated MAP kinases ERK1 and ERK2, thereby leading to impaired growth of tumor cells both in vitro and in vivo. In addition, evidence indicates that inflammatory cytokine-induced increases in MEK/ERK activity contribute to the inflammation, pain, and tissue destruction associated with rheumatoid arthritis and other inflammatory diseases.

Crystal forms of N-((R)-2,3-dihydroxypropoxy)-3,4-difluoro-2-(2-fluoro-4-iodo-phenylamino)-benzamide have been described previously. WO2002/006213 describes crystalline Forms I and II. U.S. Pat. No. 7,060,856 ("the '856 patent") describes a method of producing Form IV. The '856 patent indicates that the material produced by this method was greater than 90% Form IV (The '856 patent, Example 1). The '856 patent also states that the differential scanning calorimetry ("DSC") of the material produced shows an onset of melting at 110° C., as well as a small peak with an onset at 117° C., consistent with the material being a mixture of two forms.

WO 2006/134469 ("the '469 PCT publication") also describes a method of synthesizing N-((R)-2,3-dihydroxypropoxy)-3,4-difluoro-2-(2-fluoro-4-iodo-phenylamino)-benzamide. The '469 PCT publication reports the method yields a product conforming to the polymorphic Form IV disclosed in U.S. patent application Ser. No. 10/969,681 which issued as the '856 patent.

Compositions containing more than one polymorphic form are generally undesirable because of the potential of interconversion of one polymorphic form to another. Polymorphic interconversion can lead to differences in the effective dose or physical properties affecting processability of a drug, caused by differences in solubility or bioavailability. Thus, there is a need for a composition containing essentially pure Form IV of N-((R)-2,3-dihydroxypropoxy)-3,4-difluoro-2-(2-fluoro-4-iodo-phenylamino)-benzamide, for use in treatment of a tumor, a cancer, or a Rasopathy disorder.

BRIEF SUMMARY OF THE INVENTION

Figure 1A:
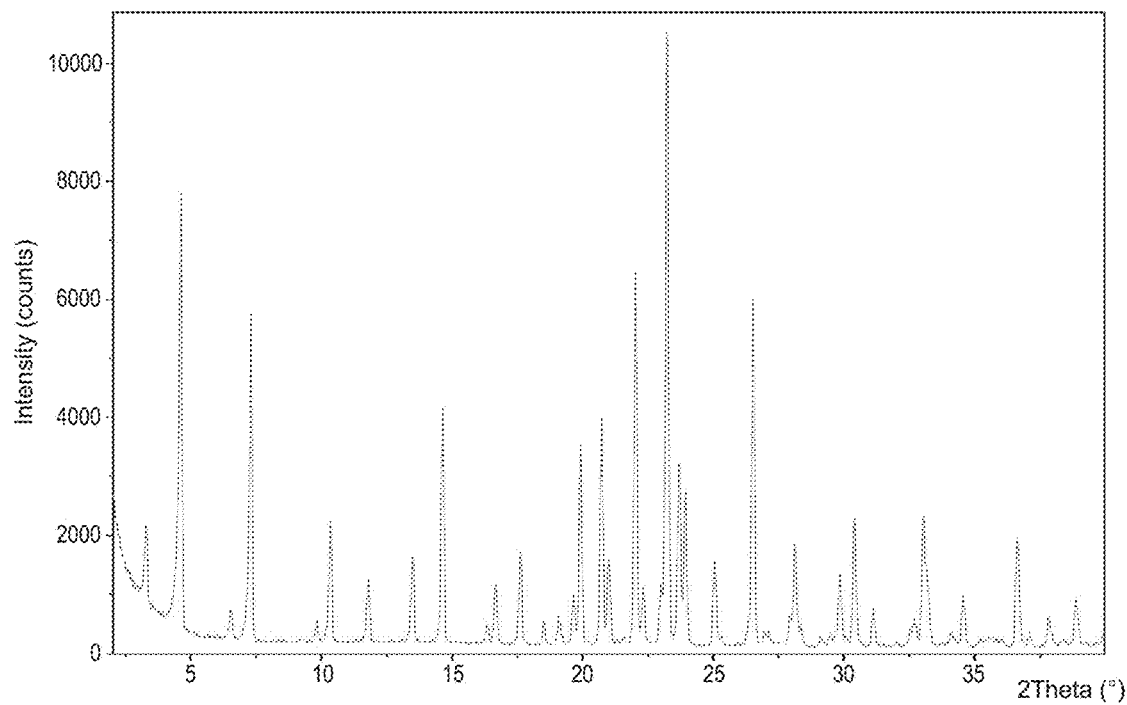
FIG. 1A is a X-ray powder diffraction pattern ("XRPD") corresponding to essentially pure crystalline Form IV of N-((R)-2,3-dihydroxypropoxy)-3,4-difluoro-2-(2-fluoro-4-iodo-phenylamino)-benzamide.

The present disclosure features useful compositions and methods to treat disorders whereby aberrant MEK1 or MEK2 activity is implicated, e.g., a cancer, a tumor, or a Rasopathy disorder, such as neurofibromatosis type 1, in a subject in need thereof.

In some aspects, the present disclosure is directed to a crystalline composition of essentially pure Form IV of N-((R)-2,3-dihydroxypropoxy)-3,4-difluoro-2-(2-fluoro-4-iodo-phenylamino)-benzamide of Formula (I)

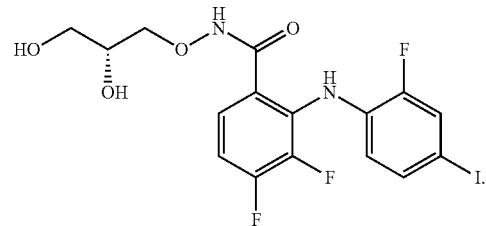 [SMILES: O=C(NOC[C@H](O)CO)c1ccc(F)c(F)c1Nc1ccc(I)cc1F]

In some aspects, the crystalline composition of essentially pure N-((R)-2,3-dihydroxypropoxy)-3,4-difluoro-2-(2-fluoro-4-iodo-phenylamino)-benzamide does not contain any amount of Form I or Form II detectable by XRPD and/or DSC.

In some aspects, the crystalline composition exhibits an XRPD pattern and/or DSC profile which is substantially unchanged after storage for 3 months at standard warehouse conditions (15° C.-25° C. and ≤65% relative humidity). In some aspects, the crystalline composition exhibits an XRPD pattern and/or DSC profile which is substantially unchanged after storage for 6 months at standard warehouse conditions (15° C.-25° C. and ≤65% relative humidity). In some aspects, the crystalline composition exhibits an XRPD pattern and/or DSC profile which is substantially unchanged after storage for 1 year at standard warehouse conditions (15° C.-25° C. and ≤65% relative humidity). In some aspects, the crystalline composition exhibits an XRPD pattern and/or DSC profile which is substantially unchanged after storage for 5 years at standard warehouse conditions (15° C.-25° C. and ≤65% relative humidity). In some aspects, the crystalline composition exhibits an XRPD pattern and/or DSC profile which is substantially unchanged after storage for 68 months at standard warehouse conditions (15° C.-25° C. and ≤65% relative humidity). In some aspects, the crystalline composition exhibits an XRPD pattern and/or DSC profile which is substantially unchanged after storage for 2140 months at standard warehouse conditions (15° C.-25° C. and ≤65% relative humidity). In some aspects, the crystalline composition exhibits an XRPD pattern and/or DSC profile which is substantially unchanged after storage for 214 years at standard warehouse conditions (15° C.-25° C. and ≤65% relative humidity).

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Göebel mirror, mirror exit slit (0.2 mm), 2.5° Soller slit, beam knife, and (b) on the diffracted beam side as follows: anti-scatter slit (8 mm) and 2.5° Soller slit, wherein samples are mounted flat on zero-background Si wafers. In some aspects, the DSC pattern is generated using a TA Instruments Q100 or Q2000 differential scanning calorimeter at a rate of temperature increase of about 15° C./min.

In some aspects, the crystalline composition contains ≤0.2% of dimeric impurity PF-00191189

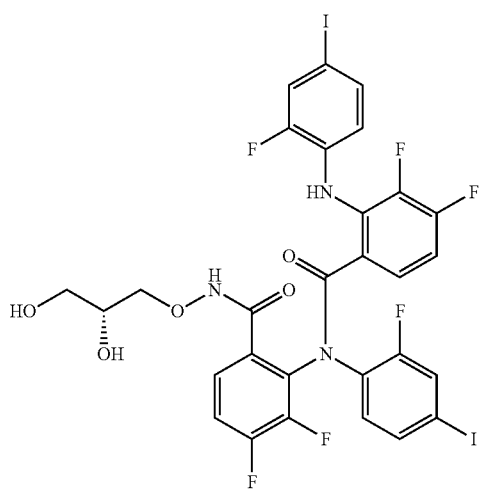

PF-00191189
Exact Mass: 856.93

In some aspects, the crystalline composition contains about 0.05% to about 0.19% by weight of dimeric impurity PF-00191189. In some aspects, the crystalline composition contains no detectable amount of dimeric impurity PF-00191189.

In some aspects, the present disclosure provides a pharmaceutical composition comprising a crystalline composition described herein and a pharmaceutically acceptable carrier. In some aspects, the pharmaceutical composition is for oral administration. In some aspects, the pharmaceutical composition is a solid dosage form. In some aspects, the pharmaceutical composition is a tablet or capsule. In some aspects, the pharmaceutical composition is a tablet.

In some aspects, the pharmaceutical composition is a capsule. In some aspects, the capsule comprises about 1 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and a gelatin capsule which encapsulates components a-d. In some aspects, the capsule comprises about 2 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components a-d. In some aspects, the capsule comprises about 5 mg of N-((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) a gelatin capsule which encapsulates components a-c.

In some aspects, at least one of the diluents is selected from the group consisting of microcrystalline cellulose, lactose, mannitol, starch, and dibasic calcium phosphate. In some aspects, at least one of the diluents is microcrystalline cellulose.

In some aspects, at least one of the disintegrants is selected from the group consisting of croscarmellose sodium, sodium starch glycolate, crospovidone, and alginic acid. In some aspects, at least one of the disintegrants is croscarmellose sodium.

In some aspects, at least one of the lubricants is selected from the group consisting of magnesium stearate, sodium stearyl fumarate, glycerol dibehenate, and talc. In some aspects, at least one of the lubricants is magnesium stearate.

In some aspects, the present disclosure provides a method of treating a cancer, a tumor, or a Rasopathy disorder comprising administering to a subject in need of such treatment a pharmaceutical composition described herein.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low grade glioma, high grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N-((R)-2,3-dihydroxypropoxy)-3,4-difluoro-2-(2-fluoro-4-iodo-phenylamino)-benzamide is administered as more than one capsule or tablet.

In some aspects, the N-((R)-2,3-dihydroxypropoxy)-3,4-difluoro-2-(2-fluoro-4-iodo-phenylamino)-benzamide is administered in a total daily dose that does not exceed 20 mg. In some aspects, the N-((R)-2,3-dihydroxypropoxy)-3,4-difluoro-2-(2-fluoro-4-iodo-phenylamino)-benzamide is administered in a total daily dose that does not exceed 10 mg. In some aspects, the N-((R)-2,3-dihydroxypropoxy)-3,4-difluoro-2-(2-fluoro-4-iodo-phenylamino)-benzamide is administered in a total daily dose that does not exceed 8 mg. In some aspects, the N-((R)-2,3-dihydroxypropoxy)-3,4-difluoro-2-(2-fluoro-4-iodo-phenylamino)-benzamide is administered in a total daily dose that does not exceed 6 mg.

In some aspects, the total daily dose of the N-((R)-2,3-dihydroxypropoxy)-3,4-difluoro-2-(2-fluoro-4-iodo-phenylamino)-benzamide is about 0.1 mg to about 20 mg. In some aspects, the total daily dose of the N-((R)-2,3-dihydroxypropoxy)-3,4-difluoro-2-(2-fluoro-4-iodo-phenylamino)-benzamide is about 2 mg. In some aspects, the total daily dose of N-((R)-2,3-dihydroxypropoxy)-3,4-difluoro-2-(2-fluoro-4-iodo-phenylamino)-benzamide is about 4 mg. In some aspects, the total daily dose of the N-((R)-2,3-dihydroxypropoxy)-3,4-difluoro-2-(2-fluoro-4-iodo-phenylamino)-benzamide is about 6 mg. In some aspects, the total daily dose of the N-((R)-2,3-dihydroxypropoxy)-3,4-difluoro-2-(2-fluoro-4-iodo-phenylamino)-benzamide is about 8 mg. In some aspects, the total daily dose of the N-((R)-2,3-dihydroxypropoxy)-3,4-difluoro-2-(2-fluoro-4-iodo-phenylamino)-benzamide is administered about 20 mg.

In some aspects, the total daily dose of the N-((R)-2,3-dihydroxypropoxy)-3,4-difluoro-2-(2-fluoro-4-iodo-phenylamino)-benzamide is administered two times daily. In some aspects, the total daily dose of the N-((R)-2,3-dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 1 mg each. In some aspects, the total daily dose of N-((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 3 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 10 mg each.

In some aspects, the N-((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N-((R)-2,3-dihydroxypropoxy)-3,4-difluoro-2-(2-fluoro-4-iodo-phenylamino)-benzamide is administered. In some aspects, the N-((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N-((R)-2,3-dihydroxypropoxy)-3,4-difluoro-2-(2-fluoro-4-iodo-phenylamino)-benzamide is administered.

In some aspects, the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N-((R)-2,3-dihydroxypropoxy)-3,4-difluoro-2-(2-fluoro-4-iodo-phenylamino)-benzamide; and (b) 7 days in which no N-((R)-2,3-dihydroxypropoxy)-3,4-difluoro-2-(2-fluoro-4-iodo-phenylamino)-benzamide is administered. In some aspects, the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N-((R)-2,3-dihydroxypropoxy)-3,4-difluoro-2-(2-fluoro-4-iodo-phenylamino)-benzamide; followed by (b) 7 consecutive days in which no N-((R)-2,3-dihydroxypropoxy)-3,4-difluoro-2-(2-fluoro-4-iodo-phenylamino)-benzamide is administered.

In some aspects, the 28-day dosing cycle is repeated up to a total of 24 consecutive 28-day dosing cycles.

In some aspects, the present disclosure provides use of a pharmaceutical composition described herein for the manufacture of a medicament for treating a tumor, a cancer, or a Rasopathy disorder.

Method of Manufacturing a Pharmaceutical Composition

In some aspects, the present disclosure provides a method of manufacturing a pharmaceutical composition, the method comprising forming a pharmaceutical composition described herein.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "mirdametinib" and "PD-0325901" refer to the single enantiomer N-((R)-2,3-dihydroxypropoxy)-3,4-difluoro-2-(2-fluoro-4-iodo-phenylamino)-benzamide.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease: delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., lung cancer or ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically acceptable material, composition, or vehicle, such as a liquid or solid excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See Remington: The Science and Practice of Pharmacy, 21st Edition, Lippincott Williams & Wilkins: Philadelphia, Pa., 2005; Handbook of Pharmaceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, Gibson Ed., CRC Press LLC: Boca Raton, Fla., 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, calcium sulfate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup).

The term "about" or "approximately" means within a range of an acceptable error for a particular value as determined by one of ordinary skill in the art, which depends in part on how the value is measured or determined. In some aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The term "crystalline," as used herein, refers to a solid-state form which consists of orderly arrangement of structural units. Different crystalline forms of the same compound, or a salt, hydrate, or solvate thereof, arise from different packing of the molecules in the solid-state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., Remington's Pharmaceutical Sciences, 18th ed., Mack Publishing, Easton Pa., 173 (1990); The United States Pharmacopeia, 23rd ed., 1843-1844 (1995) (incorporated herein by reference).

Crystalline forms are commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

The term "anhydrate" as applied to a compound refers to a crystalline form wherein the compound contains no structural water within the crystal lattice.

As used herein, the term "essentially pure" with respect to Form IV means that the composition comprising Form IV contains no detectable amount of another polymorphic form (e.g., Form I or Form II), as determined by observing no detectable differences in an XRPD and/or DSC pattern between a single Form IV crystal and the crystalline composition of N-((R)-2,3-dihydroxypropoxy)-3,4-difluoro-2-(2-fluoro-4-iodo-phenylamino)-benzamide. However, "essentially pure" Form IV of N-((R)-2,3-dihydroxypropoxy)-3,4-difluoro-2-(2-fluoro-4-iodo-phenylamino)-benzamide" can include impurities, such as, but not limited to, synthetic reactants or by-products generated during the chemical synthesis.

As used herein, the term "aberration" as applied to a gene refers to a mutation, chromosomal loss or fusion, epigenetic chemical modification, or other event which alters the sequence, level of expression, or processed mRNA sequence associated with a gene relative to the sequence, level of expression, or processed mRNA sequence associated with the wild-type gene.

It is understood that wherever aspects are described herein with the language "comprising," otherwise analogous aspects described in terms of "consisting of" and/or "consisting essentially of" are also provided.

The details of one or more aspects are set forth in the description below. Other features, objects, and advantages will be apparent from the description and from the claims.

DETAILED DESCRIPTION OF THE INVENTION

Essentially pure Form IV, compositions that are essentially pure Form IV, and methods to treat a patient in need of a therapeutic comprising administration of essentially pure Form IV are described herein.

Crystalline Composition

The present disclosure relates to an essentially pure crystalline composition of N-((R)-2,3-dihydroxypropoxy)-3,4-difluoro-2-(2-fluoro-4-iodo-phenylamino)-benzamide.

As with all pharmaceutical compounds and compositions, the chemical and physical properties of N-((R)-2,3-dihydroxypropoxy)-3,4-difluoro-2-(2-fluoro-4-iodo-phenylamino)-benzamide are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of the compound and pharmaceutical compositions comprising the compound.

A crystalline form of N-((R)-2,3-dihydroxypropoxy)-3,4-difluoro-2-(2-fluoro-4-iodo-phenylamino)-benzamide that improves upon one or more of these properties relative to other crystalline forms of the compound is desirable. Isolating pharmaceutically acceptable crystalline forms of the compound that can be manufactured and formulated on a commercial scale can be a challenge.

In some aspects, the present disclosure is directed to essentially pure Form IV of N-((R)-2,3-dihydroxypropoxy)-3,4-difluoro-2-(2-fluoro-4-iodo-phenylamino)-benzamide of Formula (I)

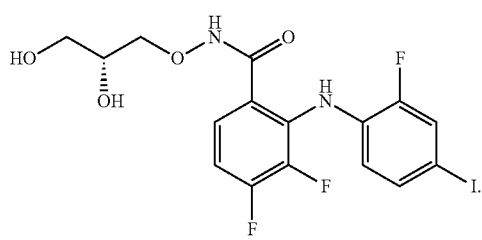

(I)

In some aspects, the crystalline composition is stable, as demonstrated by a substantially unchanged XRPD pattern and/or DSC profile over time. In some aspects, the crystalline composition exhibits an XRPD pattern and/or DSC profile which is substantially unchanged after storage for 1 month, 2 months, 3 months, 4 months, 5 months, 6 months, 7 months, 8 months, 9 months, 10 months, 1 year, 2 years, 3 years, 4 years, 5 years, 68 months, 6 years, 7 years, 8 years, 9 years, 10 years, 11 years, 140 months, 12 years, 13 years, 14 years, or 15 years at standard warehouse conditions (15° C.-25° C. and ≤65% relative humidity). In some aspects, the crystalline composition exhibits an XRPD pattern and/or DSC profile which is substantially unchanged after storage for 3 months at standard warehouse conditions (15° C.-25° C. and ≤65% relative humidity). In some aspects, the crystalline composition exhibits an XRPD pattern and/or DSC profile which is substantially unchanged after storage for 6 months at standard warehouse conditions (15° C.-25° C. and ≤65% relative humidity). In some aspects, the crystalline composition exhibits an XRPD pattern and/or DSC profile which is substantially unchanged after storage for 1 year at standard warehouse conditions (15° C.-25° C. and ≤65% relative humidity). In some aspects, the crystalline composition exhibits an XRPD pattern and/or DSC profile which is substantially unchanged after storage for 5 years at standard warehouse conditions (15° C.-25° C. and ≤65% relative humidity). In some aspects, the crystalline composition exhibits an XRPD pattern and/or DSC profile which is substantially unchanged after storage for 68 months at standard warehouse conditions (15° C.-25° C. and ≤65% relative humidity). In some aspects, the crystalline composition exhibits an XRPD pattern and/or DSC profile which is substantially unchanged after storage for ≥140 months at standard warehouse conditions (15° C.-25° C. and ≤65% relative humidity). In some aspects, the crystalline composition exhibits an XRPD pattern and/or DSC profile which is substantially unchanged after storage for ≥14 years at standard warehouse conditions (15° C.-25° C. and ≤65% relative humidity).

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows. Goëbel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers. In some aspects, the DSC pattern is generated using a TA Instruments Q100 or Q2000 differential scanning calorimeter at a rate of temperature increase of about 15° C./min.

In some aspects, the crystalline composition contains ≤0.2% of dimeric impurity PF-00191189

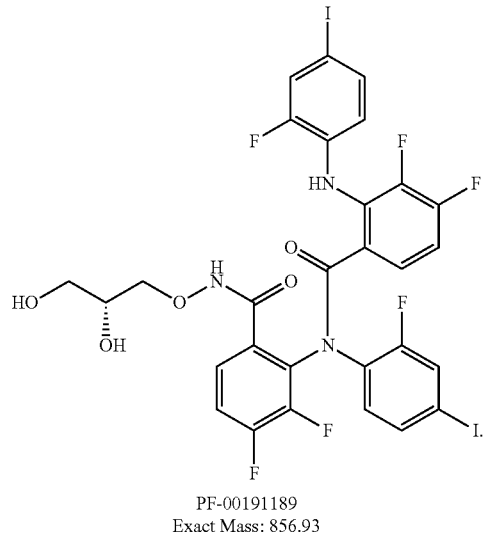

PF-00191189
Exact Mass: 856.93

In some aspects, the crystalline composition contains about 0.05% to about 0.19% by weight of dimeric impurity PF-00191189. In some aspects, the crystalline composition contains about 0.05% to about 0.15% by weight of dimeric impurity PF-00191189. In some aspects, the crystalline composition contains about 0.05% to about 0.10% by weight of dimeric impurity PF-00191189. In some aspects, the crystalline composition contains no detectable amount of dimeric impurity PF-00191189.

In some aspects, the amount of dimeric impurity PF-00191189 is determined using High Performance Liquid Chromatography ("HPLC"). In some aspects, reversed-phase liquid chromatography using an ultraviolet detector at 275 nm is used.

In some aspects, the crystalline composition exhibits a DSC profile which does not have an endothermic event with onset at about 117° C.

Figure 1B:
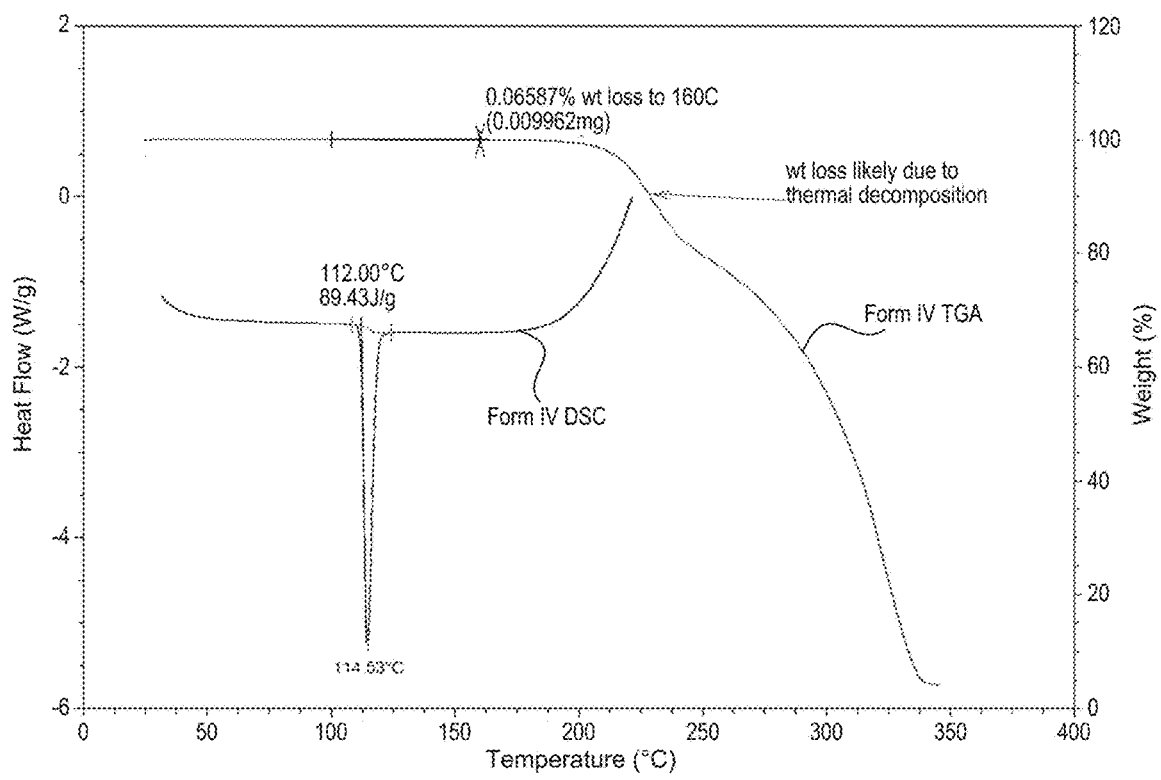
FIG. 1B is a thermogravimetric analysis thermogram ("TGA") and a differential scanning calorimetry thermogram ("DSC") corresponding to essentially pure crystalline Form IV of N-((R)-2,3-dihydroxypropoxy)-3,4-difluoro-2-(2-fluoro-4-iodo-phenylamino)-benzamide.

Form IV of N-((R)-2,3-dihydroxypropoxy)-3,4-difluoro-2-(2-fluoro-4-iodo-phenylamino)-benzamide is characterized by an XRPD pattern substantially as shown in FIG. 1A, a TGA profile substantially as shown in FIG. 1B; and/or a DSC profile substantially as shown in FIG. 1B.

Pharmaceutical Composition

In some aspects, the present disclosure provides a pharmaceutical composition comprising a crystalline composition described herein and a pharmaceutically acceptable carrier. In some aspects, the pharmaceutical composition is for oral administration. In some aspects, the pharmaceutical composition is a tablet or capsule. In some aspects, the pharmaceutical composition is a tablet. In some aspects, the pharmaceutical composition is a capsule.

In some aspects, the pharmaceutical composition comprises about 0.1 mg to about 10 mg of the crystalline composition of N-((R)-2,3-dihydroxypropoxy)-3,4-difluoro-2-(2-fluoro-4-iodo-phenylamino)-benzamide. In some aspects, the pharmaceutical composition comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg of the crystalline composition of N-((R)-2,3-dihydroxypropoxy)-3,4-difluoro-2-(2-fluoro-4-iodo-phenylamino)-benzamide. In some aspects, the pharmaceutical composition comprises about 2 mg of the crystalline composition of N-((R)-2,3-dihydroxypropoxy)-3,4-difluoro-2-(2-fluoro-4-iodo-phenylamino)-benzamide. In some aspects, the pharmaceutical composition comprises about 3 mg of the crystalline composition of N-((R)-2,3-dihydroxypropoxy)-3,4-difluoro-2-(2-fluoro-4-iodo-phenylamino)-benzamide. In some aspects, the pharmaceutical composition comprises about 4 mg of the crystalline composition of N-((R)-2,3-dihydroxypropoxy)-3,4-difluoro-2-(2-fluoro-4-iodo-phenylamino)-benzamide. In some aspects, the pharmaceutical composition comprises about 5 mg of the crystalline composition of N-((R)-2,3-dihydroxypropoxy)-3,4-difluoro-2-(2-fluoro-4-iodo-phenylamino)-benzamide.

In some aspects, the pharmaceutical composition comprises about 0.25 wt/wt % to about 7 wt/wt % of the crystalline composition of N-((R)-2,3-dihydroxypropoxy)-3,4-difluoro-2-(2-fluoro-4-iodo-phenylamino)-benzamide described herein. In some aspects, the pharmaceutical composition comprises about 0.25 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, or about 7 wt/wt % of the crystalline composition of N-((R)-2,3-dihydroxypropoxy)-3,4-difluoro-2-(2-fluoro-4-iodo-phenylamino)-benzamide described herein. In some aspects, the pharmaceutical composition comprises about 0.5 wt/wt % of the crystalline composition of N-((R)-2,3-dihydroxypropoxy)-3,4-difluoro-2-(2-fluoro-4-iodo-phenylamino)-benzamide described herein. In some aspects, the pharmaceutical composition comprises about 0.8 wt/wt % of the crystalline composition of N-((R)-2,3-dihydroxypropoxy)-3,4-difluoro-2-(2-fluoro-4-iodo-phenylamino)-benzamide described herein.

In some aspects, the pharmaceutical composition comprises one or more diluents. In some aspects, the pharmaceutical composition comprises about 70 wt/wt % to about 95 wt/wt % of one or more diluents. In some aspects, the pharmaceutical composition comprises about 85 wt/wt % to about 95 wt/wt % of one or more diluents. In some aspects, the pharmaceutical composition comprises about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, or about 95 wt/wt % of one or more diluents. In some aspects, the pharmaceutical composition comprises about 90 wt/wt % of one or more diluents. In some aspects, the pharmaceutical composition comprises about 93 wt/wt % of one or more diluents.

In some aspects, at least one of the diluents is selected from the group consisting of microcrystalline cellulose, lactose, mannitol, starch, and dibasic calcium phosphate. In some aspects, at least one of the diluents is microcrystalline cellulose. In some aspects, the diluent is microcrystalline cellulose.

In some aspects, the pharmaceutical composition comprises about 70 wt/wt % to about 95 wt/wt % microcrystalline cellulose. In some aspects, the pharmaceutical composition comprises about 85 wt/wt % to about 95 wt/wt % microcrystalline cellulose. In some aspects, the pharmaceutical composition comprises about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, or about 95 wt/wt % microcrystalline cellulose. In some aspects, the pharmaceutical composition comprises about 90 wt/wt % microcrystalline cellulose. In some aspects, the pharmaceutical composition comprises about 93 wt/wt % microcrystalline cellulose.

In some aspects, the pharmaceutical composition comprises about 3.5 wt/wt % to about 6 wt/wt % of one or more disintegrants. In some aspects, the pharmaceutical composition comprises about 3.5 wt/wt % about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, or about 6.0 wt/wt % of one or more disintegrants. In some aspects, the pharmaceutical composition comprises about 5 wt/wt % of one or more disintegrants.

In some aspects, at least one of the disintegrants is selected from the group consisting of croscarmellose sodium, sodium starch glycolate, crospovidone, and alginic acid. In some aspects, at least one of the disintegrants is croscarmellose sodium. In some aspects, the disintegrant is croscarmellose sodium. In some aspects, the pharmaceutical composition comprises about 3.5 wt/wt % to about 6 wt/wt % croscarmellose sodium. In some aspects, the pharmaceutical composition comprises about 3.5 wt/wt % about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, or about 6.0 wt/wt % croscarmellose sodium. In some aspects, the pharmaceutical composition comprises about 5 wt/wt % croscarmellose sodium.

In some aspects, the pharmaceutical composition comprises 0 wt/wt % to about 2 wt/wt % of one or more lubricants. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, or about 2 wt/wt % of one or more lubricants. In some aspects, the pharmaceutical composition comprises about 1 wt/wt % of one or more lubricants.

In some aspects, at least one of the lubricants is selected from the group consisting of magnesium stearate, sodium stearyl fumarate, glycerol dibehenate, and talc. In some aspects, at least one of the lubricants is magnesium stearate. In some aspects, the lubricant is magnesium stearate. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, or about 2 wt/wt % magnesium stearate. In some aspects, the pharmaceutical composition comprises 0 wt/wt % magnesium stearate. In some aspects, the pharmaceutical composition comprises about 1 wt/wt % magnesium stearate.

In some aspects, the pharmaceutical composition is a capsule. In some aspects, the capsule comprises about 1 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 2 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 3 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 4 mg of N-((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 5 mg of N-((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the crystalline composition of N-((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) a gelatin capsule which encapsulates components a-c.

Methods of Treatment

In some aspects, the present disclosure provides a method of treating a tumor, a cancer, or a Rasopathy disorder comprising administering to a subject in need of such treatment a pharmaceutical composition described herein.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low grade glioma, high grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N-((R)-2,3-dihydroxypropoxy)-3,4-difluoro-2-(2-fluoro-4-iodo-phenylamino)-benzamide is administered as more than one capsule or tablet. For example, a dose of 3 mg of the N-((R)-2,3-dihydroxypropoxy)-3,4-difluoro-2-(2-fluoro-4-iodo-phenylamino)-benzamide can be administered as two capsules—one containing 2 mg and the other containing 1 mg or as three capsules each containing 1 mg.

In some aspects, the N-((R)-2,3-dihydroxypropoxy)-3,4-difluoro-2-(2-fluoro-4-iodo-phenylamino)-benzamide is provided in an amount of about 0.1 mg to about 20 mg per dose of the pharmaceutical compositions described herein. In some aspects, the N-((R)-2,3-dihydroxypropoxy)-3,4-difluoro-2-(2-fluoro-4-iodo-phenylamino)-benzamide is provided in an amount of about 0.1 mg, about 0.2 mg, about 0.3 mg, about 0.4 mg, about 0.5 mg, about 0.6 mg, about 0.7 mg, about 0.8 mg, about 0.9 mg, about 8 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg per dose. In some aspects, the N-((R)-2,3-dihydroxypropoxy)-3,4-difluoro-2-(2-fluoro-4-iodo-phenylamino)-benzamide is provided in an amount of about 1 mg per dose. In some aspects, the N-((R)-2,3-dihydroxypropoxy)-3,4-difluoro-2-(2-fluoro-4-iodo-phenylamino)-benzamide is provided in an amount of about 2 mg per dose. In some aspects, the N-((R)-2,3-dihydroxypropoxy)-3,4-difluoro-2-(2-fluoro-4-iodo-phenylamino)-benzamide is provided in an amount of about 3 mg per dose. In some aspects, the N-((R)-2,3-dihydroxypropoxy)-3,4-difluoro-2-(2-fluoro-4-iodo-phenylamino)-benzamide is provided in an amount of about 4 mg per dose. In some aspects, the N-((R)-2,3-dihydroxypropoxy)-3,4-difluoro-2-(2-fluoro-4-iodo-phenylamino)-benzamide is provided in an amount of about 10 mg per dose.

In some aspects, the pharmaceutical composition comprising N-((R)-2,3-dihydroxypropoxy)-3,4-difluoro-2-(2-fluoro-4-iodo-phenylamino)-benzamide is administered one time, two times, three times, or four times per day. In some aspects, the total daily dose of the N-((R)-2,3-dihydroxypropoxy)-3,4-difluoro-2-(2-fluoro-4-iodo-phenylamino)-benzamide is administered two times per day.

In some aspects, if the N-((R)-2,3-dihydroxypropoxy)-3,4-difluoro-2-(2-fluoro-4-iodo-phenylamino)-benzamide is to be administered more than one time a day, the total daily dose of the N-((R)-2,3-dihydroxypropoxy)-3,4-difluoro-2-(2-fluoro-4-iodo-phenylamino)-benzamide can be divided so the patient receives equal doses at each administration. For example, if the total daily dose of the N-((R)-2,3-dihydroxypropoxy)-3,4-difluoro-2-(2-fluoro-4-iodo-phenylamino)-benzamide is to be 4 mg administered two times per day, the patient can receive 2 mg (e.g., as two 1 mg capsules) in the morning and 2 mg (e.g., as one 2 mg capsule) in the evening.

In some aspects, if the N-((R)-2,3-dihydroxypropoxy)-3,4-difluoro-2-(2-fluoro-4-iodo-phenylamino)-benzamide is to be administered more than one time a day, the total daily dose of the N-((R)-2,3-dihydroxypropoxy)-3,4-difluoro-2-(2-fluoro-4-iodo-phenylamino)-benzamide can be divided so the patient receives different doses at each administration. For example, if the total daily dose of the N-((R)-2,3-dihydroxypropoxy)-3,4-difluoro-2-(2-fluoro-4-iodo-phenylamino)-benzamide is to be 4 mg administered two times per day, the patient can receive 1 mg (e.g., as one 1 mg capsule) in the morning and 3 mg (e.g., as one 1 mg capsule and one 2 mg capsule) in the evening.

In some aspects, the present disclosure provides a method of treating a tumor, a cancer, or a Rasopathy disorder comprising administering to a patient in need of such treatment a pharmaceutical composition described herein, wherein the total daily dose of the N-((R)-2,3-dihydroxypropoxy)-3,4-difluoro-2-(2-fluoro-4-iodo-phenylamino)-benzamide is administered two times daily of about 0.1 mg to about 10 mg each.

In some aspects, the crystalline composition of N-((R)-2,3-dihydroxypropoxy)-3,4-difluoro-2-(2-fluoro-4-iodo-phenylamino)-benzamide is administered via a pharmaceutical composition described herein, wherein the N-((R)-2,3-dihydroxypropoxy)-3,4-difluoro-2-(2-fluoro-4-iodo-phenylamino)-benzamide is provided at a total daily dose that does not exceed 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In some aspects, the N-((R)-2,3-dihydroxypropoxy)-3,4-difluoro-2-(2-fluoro-4-iodo-phenylamino)-benzamide is administered in a total daily dose that does not exceed 20 mg. In some aspects, the N-((R)-2,3-dihydroxypropoxy)-3,4-difluoro-2-(2-fluoro-4-iodo-phenylamino)-benzamide is administered in a total daily dose that does not exceed 15 mg. In some aspects, the N-((R)-2,3-dihydroxypropoxy)-3,4-difluoro-2-(2-fluoro-4-iodo-phenylamino)-benzamide is administered in a total daily dose that does not exceed 12 mg. In some aspects, the N-((R)-2,3-dihydroxypropoxy)-3,4-difluoro-2-(2-fluoro-4-iodo-phenylamino)-benzamide is administered in a total daily dose that does not exceed 10 mg. In some aspects, the N-((R)-2,3-dihydroxypropoxy)-3,4-difluoro-2-(2-fluoro-4-iodo-phenylamino)-benzamide is administered in a total daily dose that does not exceed 8 mg. In some aspects, the N-((R)-2,3-dihydroxypropoxy)-3,4-difluoro-2-(2-fluoro-4-iodo-phenylamino)-benzamide is administered in a total daily dose that does not exceed 6 mg. In some aspects, the N-((R)-2,3-dihydroxypropoxy)-3,4-difluoro-2-(2-fluoro-4-iodo-phenylamino)-benzamide is administered in a total daily dose that does not exceed 2 mg. In some aspects, the N-((R)-2,3-dihydroxypropoxy)-3,4-difluoro-2-(2- fluoro-4-iodo-phenylamino)-benzamide is administered in a total daily dose that does not exceed 1 mg.

In some aspects, the present disclosure provides a method of treating a tumor, a cancer, or a Rasopathy disorder comprising administering to a patient in need of such treatment a pharmaceutical composition described herein, wherein the total daily dose of the N-((R)-2,3-dihydroxypropoxy)-3,4-difluoro-2-(2-fluoro-4-iodo-phenylamino)-benzamide is administered once daily at a dose of about 0.1 mg to about 20 mg.

In some aspects, the total daily dose of the N-((R)-2,3-dihydroxypropoxy)-3,4-difluoro-2-(2-fluoro-4-iodo-phenylamino)-benzamide is administered once daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In some aspects, the total daily dose of the N-((R)-2,3-dihydroxypropoxy)-3,4-difluoro-2-(2-fluoro-4-iodo-phenylamino)-benzamide is administered once daily at a dose of about 1 mg. In some aspects, the total daily dose of the N-((R)-2,3-dihydroxypropoxy)-3,4-difluoro-2-(2-fluoro-4-iodo-phenylamino)-benzamide is administered once daily at a dose of about 2 mg. In some aspects, the total daily dose of the N-((R)-2,3-dihydroxypropoxy)-3,4-difluoro-2-(2-fluoro-4-iodo-phenylamino)-benzamide is administered once daily at a dose of about 3 mg. In some aspects, the total daily dose of N-((R)-2,3-dihydroxypropoxy)-3,4-difluoro-2-(2-fluoro-4-iodo-phenylamino)-benzamide is administered once daily at a dose of about 4 mg. In some aspects, the total daily dose of the N-((R)-2,3-dihydroxypropoxy)-3,4-difluoro-2-(2-fluoro-4-iodo-phenylamino)-benzamide is administered once daily at a dose of about 5 mg. In some aspects, the total daily dose of the N-((R)-2,3-dihydroxypropoxy)-3,4-difluoro-2-(2-fluoro-4-iodo-phenylamino)-benzamide is administered once daily at a dose of about 6 mg. In some aspects, the total daily dose of the N-((R)-2,3-dihydroxypropoxy)-3,4-difluoro-2-(2-fluoro-4-iodo-phenylamino)-benzamide is administered once daily at a dose of about 7 mg. In some aspects, the total daily dose of the N-((R)-2,3-dihydroxypropoxy)-3,4-difluoro-2-(2-fluoro-4-iodo-phenylamino)-benzamide is administered once daily at a dose of about 8 mg. In some aspects, the total daily dose of the N-((R)-2,3-dihydroxypropoxy)-3,4-difluoro-2-(2-fluoro-4-iodo-phenylamino)-benzamide is administered once daily at a dose of about 9 mg. In some aspects, the total daily dose of the N-((R)-2,3-dihydroxypropoxy)-3,4-difluoro-2-(2-fluoro-4-iodo-phenylamino)-benzamide is administered once daily at a dose of about 10 mg. In some aspects, the total daily dose of the N-((R)-2,3-dihydroxypropoxy)-3,4-difluoro-2-(2-fluoro-4-iodo-phenylamino)-benzamide is administered once daily at a dose of about 11 mg. In some aspects, the total daily dose of the N-((R)-2,3-dihydroxypropoxy)-3,4-difluoro-2-(2-fluoro-4-iodo-phenylamino)-benzamide is administered once daily at a dose of about 12 mg. In some aspects, the total daily dose of the N-((R)-2,3-dihydroxypropoxy)-3,4-difluoro-2-(2-fluoro-4-iodo-phenylamino)-benzamide is administered once daily at a dose of about 13 mg. In some aspects, the total daily dose of the N-((R)-2,3-dihydroxypropoxy)-3,4-difluoro-2-(2-fluoro-4-iodo-phenylamino)-benzamide is administered once daily at a dose of about 14 mg. In some aspects, the total daily dose of the N-((R)-2,3-dihydroxypropoxy)-3,4-difluoro-2-(2-fluoro-4-iodo-phenylamino)-benzamide is administered once daily at a dose of about 15 mg. In some aspects, the total daily dose of the N-((R)-2,3-dihydroxypropoxy)-3,4-difluoro-2-(2-fluoro-4-iodo-phenylamino)-benzamide is administered once daily at a dose of about 16 mg. In some aspects, the total daily dose of the N-((R)-2,3-dihydroxypropoxy)-3,4-difluoro-2-(2-fluoro-4-iodo-phenylamino)-benzamide is administered once daily at a dose of about 17 mg. In some aspects, the total daily dose of the N-((R)-2,3-dihydroxypropoxy)-3,4-difluoro-2-(2-fluoro-4-iodo-phenylamino)-benzamide is administered once daily at a dose of about 18 mg. In some aspects, the total daily dose of the N-((R)-2,3-dihydroxypropoxy)-3,4-difluoro-2-(2-fluoro-4-iodo-phenylamino)-benzamide is administered once daily at a dose of about 19 mg. In some aspects, the total daily dose of the N-((R)-2,3-dihydroxypropoxy)-3,4-difluoro-2-(2-fluoro-4-iodo-phenylamino)-benzamide is administered once daily at a dose of about 20 mg.

In some aspects, the total daily dose of the N-((R)-2,3-dihydroxypropoxy)-3,4-difluoro-2-(2-fluoro-4-iodo-phenylamino)-benzamide is administered two times daily. In some aspects, the total daily dose of the N-((R)-2,3-dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, or about 10 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 0.25 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 0.5 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 1 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 3 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 5 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 6 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 7 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 8 mg each. In some aspects, the total daily dose of the N-((R)-2,3-dihydroxypropoxy)-3,4-difluoro-2-(2-fluoro-4- iodo-phenylamino)-benzamide is administered two times daily at a dose of about 9 mg each. In some aspects, the total daily dose of the N-((R)-2,3-dihydroxypropoxy)-3,4-difluoro-2-(2-fluoro-4-iodo-phenylamino)-benzamide is administered two times daily at a dose of about 10 mg each.

In some aspects, the N-((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N-((R)-2,3-dihydroxypropoxy)-3,4-difluoro-2-(2-fluoro-4-iodo-phenylamino)-benzamide is administered. In some aspects, the N-((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N-((R)-2,3-dihydroxypropoxy)-3,4-difluoro-2-(2-fluoro-4-iodo-phenylamino)-benzamide is administered.

In some aspects, the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N-((R)-2,3-dihydroxypropoxy)-3,4-difluoro-2-(2-fluoro-4-iodo-phenylamino)-benzamide; and (b) 7 days in which no N-((R)-2,3-dihydroxypropoxy)-3,4-difluoro-2-(2-fluoro-4-iodo-phenylamino)-benzamide is administered. In some aspects, the of N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N-((R)-2,3-dihydroxypropoxy)-3,4-difluoro-2-(2-fluoro-4-iodo-phenylamino)-benzamide; followed by (b) 7 consecutive days in which no N-((R)-2,3-dihydroxypropoxy)-3,4-difluoro-2-(2-fluoro-4-iodo-phenylamino)-benzamide is administered.

In some aspects, the N-((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

In some aspects, the 28-day dosing cycle is repeated up to a total of 24 consecutive 28-day dosing cycles.

In some aspects, the present disclosure provides use of a pharmaceutical composition described herein for the manufacture of a medicament for treating a cancer, a tumor, or a Rasopathy disorder.

EXAMPLES

| Time (minutes) | 0 | 15 | 40 | 45 | 46 |
|---|---|---|---|---|---|
| % mobile phase B | 70 | 70 | 100 | 100 | 70 |

Example 1: Production of Essentially Pure Form IV

Lab Scale Production of Essentially Pure Form IV 2 kg PD-0325901 has been prepared using the below convergent synthesis scheme starting from commercially available 2,3,4-Trifluorobenzoic Acid (TFBA), 2-Fluoro-4-Iodoaniline (FIA) and chiral S-Glycerol Acetonide (SGA)

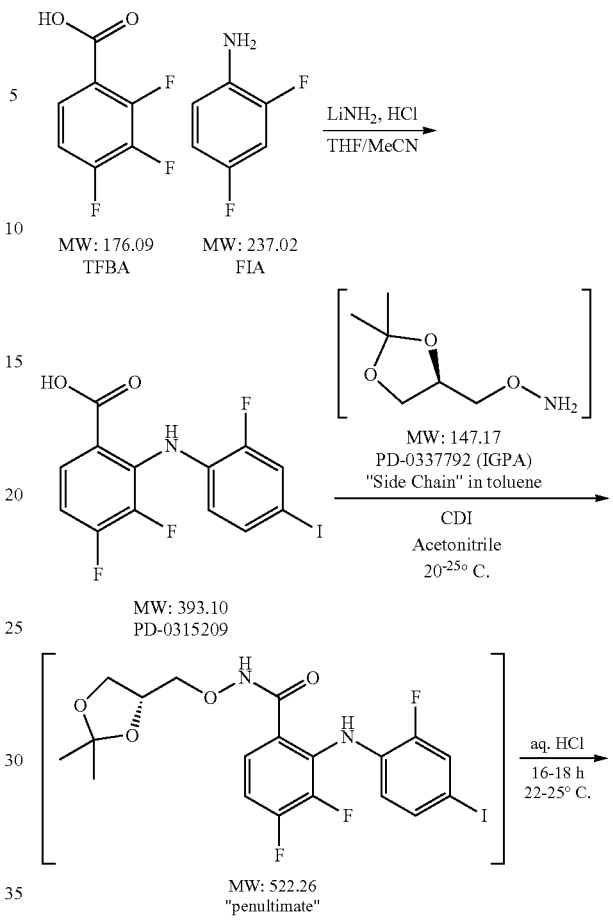

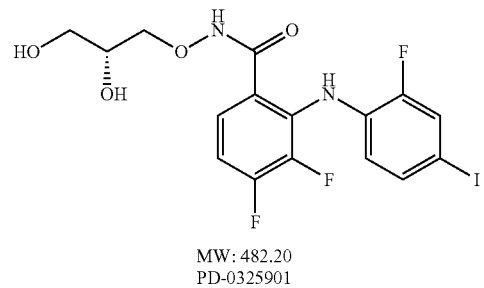

PD-0337792 "Side Chain" preparation

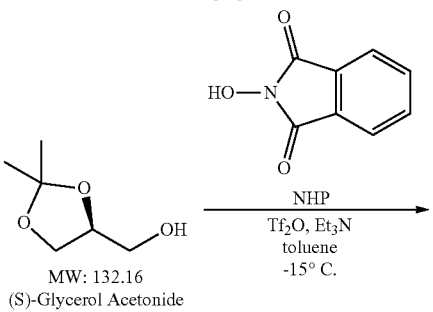

-continued

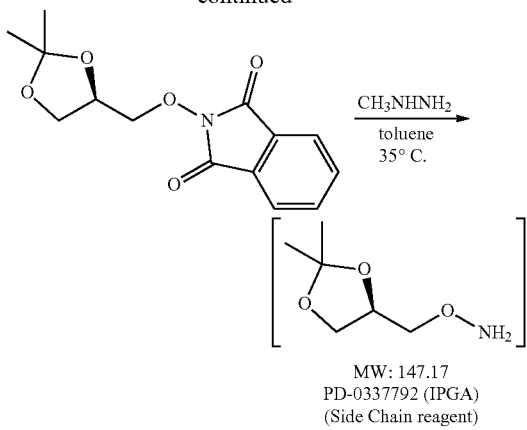

MW: 147.17
PD-0337792 (IPGA)
(Side Chain reagent)

Step 1: Preparation of "Side Chain", PD-0337792

All reactions were performed in toluene other than otherwise stated. Triflic anhydride gave the best yield.

TABLE 1

Coupling Agents for Step 1

| Entry No. | Coupling Agent | Yield | Notes |
|---|---|---|---|
| 1 | Mesyl Chloride | did not react | |
| 2 | Benzylchloride | 27 | Had to heat 70° C. for 166 hr |
| 3 | 4-fluorobenzen-sulfonylchloride | 27 | Ran 93 hrs. at 70° C. |
| 4 | 4-chlorobenzen-sulfonylchloride | 35 | Complete after 68 hrs. 50° C. |
| 5 | Tosyl Chloride | 36 | Had to heat to 70° C. for 164 hrs |
| 6 | Benzyl chloride | 52 | study solvent effects: DMF, DMSO, NMP - all similar DMSO fastest all complete after 110 hrs., heated to 70° C. after 66 hrs. |
| 7 | Triflic anhydride | 91 | Cooled to −74° C. |

Recognizing that triflate gave the highest yield, the possibility of eliminating the cryogenic conditions was investigated, set possibly due to stability concerns of the "methanesulfonate" intermediate. The following experiments suggest no significant yield loss for experiments run at −20'° C.

TABLE 2

Yield of Coupling Reaction

| Experimental Description* | Hold time after TFMSA addn. | Yield (Alcohol to IPGAP) |
|---|---|---|
| 1.07 equiv. NHP | 15 min. | 85% |
| 1.07 equiv. NHP | 2 hours | 86% |
| 1.77 equiv. NHP | 2 hours | 72% |
| 1.07 equiv. NHP (reverse addition) | 1 hours | 91% |

*2 g (1 eq.) SGA in 16 ml toluene was treated with triflic anhydride, trifluoromethanesulfonic acid (TFMSA) (4.2 g, 1.002 equiv.) at −20° C. and then stirred for a prescribed time prior to solid N-hydroxyphthalimide (NHP) addition or transfer to a flask containing solid NHP.

The data presented above suggest no detrimental effect was observed after prolonged stirring of the "trifluoromethane sulfonate" intermediate prior to the N-hydroxyphthalimide addition. Reverse addition of intermediate mixture to solid NHP appears to give the highest yield.

An additional advantage of the triflate usage was easy removal of the $Et_3N$ triflate salts side product simply by water wash. This resulted in highly pure N-hydroxyphthalimide-protected alcohol, IPGAP (PD-0333760) in Toluene, which can be isolated as crystals or carried through to the final deprotection reaction.

Both aqueous and anhydrous ammonia base were examined as deprotecting agents. The results were both successful. The phthalimide side product was simply filtered out from solution of product (PD-0337792) in toluene when anhydrous ammonia was used. Similarly, it was filtered out from the solution after performing azeotropic water removal from toluene when aqueous ammonia (28% solution) was used. Anhydrous ammonia however, requires the reaction to be performed at high-pressure containment. Experiments conducted by sparging the ammonia gas gave acceptable yields; however, they required large volumes and use of a cryogenic condenser (to avoid gas from escaping the reactor headspace).

TABLE 3

Yields for base deprotection

| Reagent | Yield* |
|---|---|
| Methyl hydrazine | 85-95% |
| Anhydrous $NH_3$ (sparged) | 78-90% |
| Anhydrous $NH_3$ (50 psi) | 80-97% |
| Aqueous $NH_3$ | 90-97% |

*from PD-0333760

Step 2: Fluoride Displacement

Examination of the reaction in an automated reactor reveals that the reaction is essentially dosed-controlled after the initiation period. Increasing the amount of lithium amide and increased agitation rate appear to shorten the induction time. The addition of water was shown to prolong the induction time. However, it is not clear whether it is due to lithium hydroxide formation.

Induction time is increased when 0.1 equivalent $H_2O$ was added. The trend was reversed however when 0.1 equivalent lithium hydroxide was added. Induction times were decreased upon increasing lithium amide equivalents and agitation.

Step 3: Amide Coupling and Deprotection

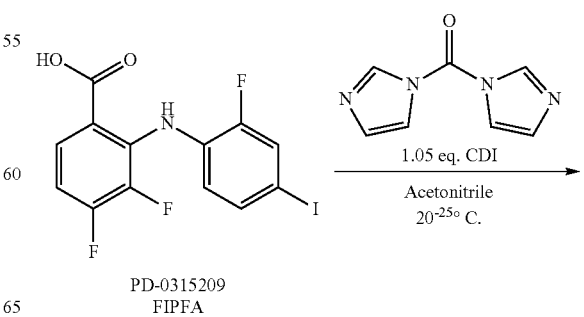

PD-0315209
FIPFA

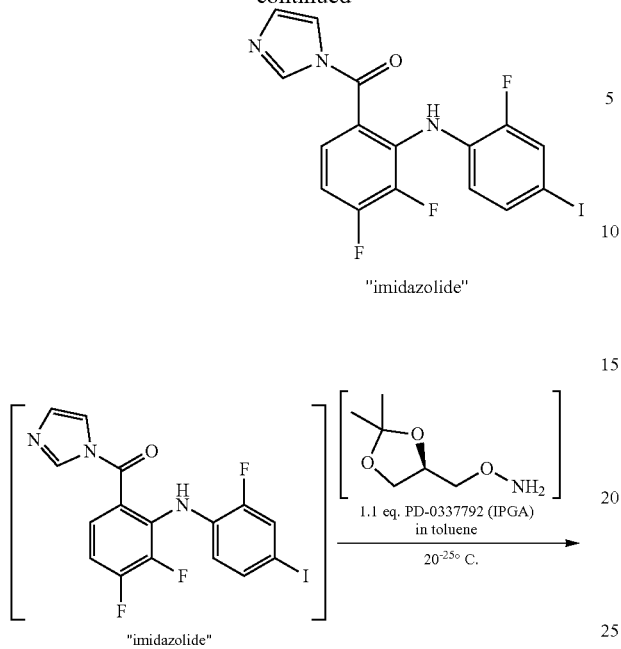

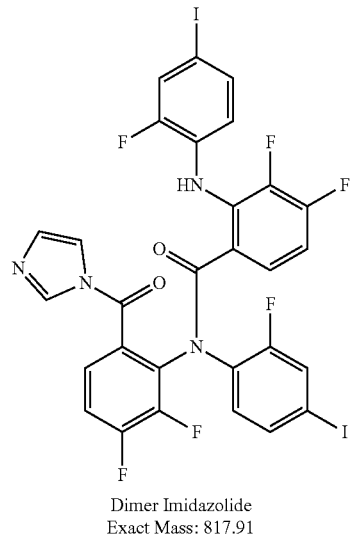

Dimer Imidazolide
Exact Mass: 817.91

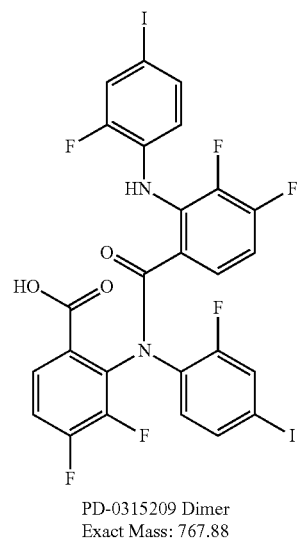

PD-0315209 Dimer
Exact Mass: 767.88

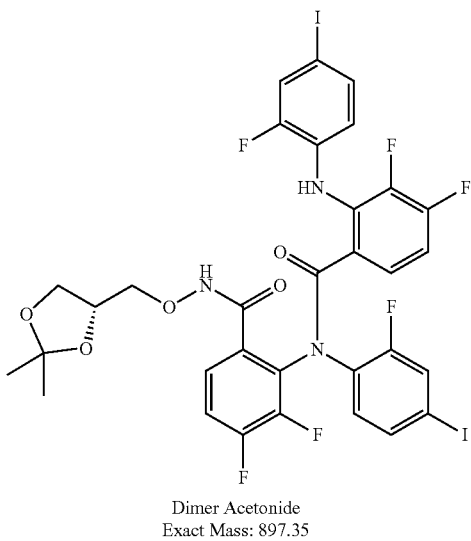

Dimer Acetonide
Exact Mass: 897.35

CDI-assisted coupling of PD-0315209 acid and sidechain reagent followed by the acid (with aqueous HCl) hydrolysis consistently yielded good results in the laboratory. The development focus of this step was to ensure that impurity levels are within the specification limit. The known impurities in the final isolated diol product are excess PD-0315209 acid, dimeric impurities and chiral impurities. The chiral impurities are controlled by limiting the R-enantiomer in the starting s-glycerol acetonide. Elevated levels of dimeric impurity (d) has been known to cause difficulties in the polymorph transformation step. The dimeric impurity is formed initially by the reaction of imidazole (CDI-activated acid) in the presence of excess acid PD-0315209 forming dimer (a) and possibly (b) which are then carried through in the subsequent IPGA coupling and acid hydrolysis steps forming dimer (c) and (d), respectively. Impurity d is referred to as PF-00191189.

-continued (d)

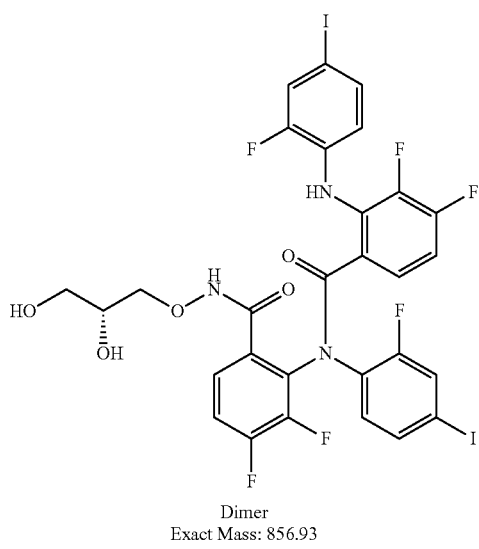

Dimer
Exact Mass: 856.93

The reaction can be easily carried out in the laboratory either by charging both solids, FIPFA and CDI, followed by solvent (acetonitrile) or charging solids CDI into a slurry of FIPFA in acetonitrile. None of the solids is initially soluble in acetonitrile. The acid activation reaction was fast (almost instantaneous), forming highly soluble imidazolide product that turned the slurry into a clear homogenous solution while $CO_2$ gas evolution occurs.

Lab experiments generally resulted in impurity levels under 3%, which can be completely removed by the subsequent recrystallization from a 3-5% ethanol-toluene system. An additional recrystallization was performed in the few instances where the impurity level was above 0.3%. Table 4 shows selected results of lab experiments where elevated levels of impurities were observed and how they were removed in the subsequent recrystallization. The crude PD-0325901 was obtained using the acetonitrile/toluene system and the purified product was recrystallized from a 5% ethanol/toluene system. Entries no. 4 and 5 used additional solvent to ensure impurity removal with entry 5 requiring two recrystallizations in order to achieve a level of "ND" in the polymorph transformation. The 8-10 ml/g crude crystallization volume was chosen to limit product loss while maintaining a filterable slurry and ensuring removal of impurities.

A scale up procedure that would give tolerable levels of impurities prior to the polymorph transformation (<0.3%), without losing too much product in the recrystallization was developed considering the solid CDI addition rate. Fast addition is preferred to minimize impurity formation; however, the addition needs to be performed at a rate that ensures safely venting of the evolved $CO_2$.

A half portion of solid CDI was initially added to the PD-0325901 acid, followed by solvent addition. The remaining CDI was added then through a hopper in less than 30 minutes to ensure that the impurity levels were below 3%.

Polymorph Transformation

Three polymorphic forms of PD-0325901 are characterized below. Form I has the highest melting point (~117° C.) and is enantiotropically related to Form IV (m.p. 112° C.), which is the more stable form below the estimated transition temperature of 73° C. Form II is the low melting form (m.p. ~85° C.).

TABLE 5

Crystal Forms Melting Points and Heat of Fusions

|  | Melting Point, ° C. | Heat of Fusion, DHf (J/g) |
| --- | --- | --- |
| Form I | 117 | 85 |
| Form II | 90 | 70 |
| Form IV | 112 | 94 |

Most of the polymorph transformation experiments were performed using highly pure PD-0325901 containing various forms and generally exhibited a low melting point below 80° C. as the results of an efficient EtOH/Toluene recrystallization following the crude crystal isolation directly from the reaction mixture. These various polymorphs were completely dissolved in EtOH and subsequently precipitated by adding water (20 volumes) in a 15-to-60 minute period at 20-25° C. Analysis of the solids sampled at less than 2 hours stirring show complete polymorph transformation to Form IV. The only failure occurred when water was added almost immediately in one portion to a solution of PD-0325901 in EtOH (4 vol.). In this case, the undesired polymorph Form I was obtained exclusively.

One anomaly in the standard procedure was observed. One lot produced mixed polymorphs but had no detectable level of impurity after recrystallization. The corrective procedure for this case includes transforming the low melting forms (Form II) to all Form I at temperatures close to or above 73° C. followed by a slow (~4 h period) cooling to 20° C.

TABLE 4

Purification of PD-0325901

| Entry No | Tot. Imp. In reaction mixture | Tot. Imp. In isolated Crude PD-0325901 | Recrystallization Vol (ml/g crude) | Tot. Imp. Purified PD-0325901 | Final assay (after polymorph transformation) |
| --- | --- | --- | --- | --- | --- |
| 1 | 2.4% | ND | 8 | ND | 99.8% |
| 2 | 10.5% | 2% | 8 | ND | 99.6% |
| 3 | 6% | 1% | 8 | ND | 99.4% |
| 4 | 10% | 3.2% | 15 | ND | 98.6% |
| 5 | 70% | 12% | 13 | 0.6% | 98.4%* |

The EtOH/Water system produces an efficient polymorph transformation. The recrystallized (purified) PD-0325901, which initially consisted of enantiotropic polymorphs Form I (m.p. ~117° C.) and Form IV (m.p. ~112° C.) was completely transformed to Form IV.

Pilot Plant Preparation of Essentially Pure Form IV

Step 1: Preparation of "Side Chain", PD-0337792

14.4 kg alcohol (chemical purity 99.4%, optical purity 99.6% enantiomeric excess) was converted to 97.5 kg 9.7% w/w PD-0337792 (IPGA) solution in toluene (overall yield ~60%). The triflate activation was performed in the 200 L reactor by maintaining temperatures under −20° C. during triflic anhydride addition. The resulting activated alcohol was then transferred to a 400 L reactor containing solid N-hydroxypthalimide (NHP) and the reaction was allowed to occur at ambient temperature to completion. The final base de-protection was performed by adding aqueous ammonia (~28% soln, 5 equiv., 34 kg). After reaction completion, water was removed by distillation from toluene, and the resulting solid side product was filtered out to yield the product solution.

Step 2: Preparation of PD-0315209

The process yielded 21.4 kg (99.4% w/w assay), which is 80% of theoretical from starting materials 2,3,4-trifluorobenzoic acid (12 kg, 1 eq.) and 2-fluoro-4-iodoaniline (16.4 kg, 1.02 eq.) with lithium amide base (5 kg, 3.2 eq.). The reaction was initiated by adding 5% of total solution of TFBA and FIA into lithium amide slurry at 50° C. This reaction demonstrated a minimal initiation period of ~10 minutes, which was observed by color change and slight exotherm. The remaining TFBA/FIA solution in THF was slowly added through a pressure can in an hour while maintaining the reaction temperatures within 45-55° C. There was no appreciable pressure rise (due to ammonia gas release) observed during the entire operation.

Step 3: Preparation of PD-0325901

A modification was made to the CDI charging to mitigate potential gas generation. Two equal portions of CDI were added into solid FIPFA before and after solvent addition (through a shot loader). The timing between the two solid CDI additions (4.6 kg each) should not exceed 30 minutes. Then two intermediate filter cakes were dissolved with ethanol. The excess ethanol was distilled and replaced with toluene to approximately 5% v/v ethanol prior to PD-0325901 recrystallization. Lab studies suggested that the crystallization from toluene and acetonitrile and recrystallization from ethanol in toluene would not be able to reduce impurities which is essential for the polymorph transformation. The presence of a dimeric impurity (PF-00191189) at a level greater than 0.2% has been known to result in the formation of undesired polymorph.

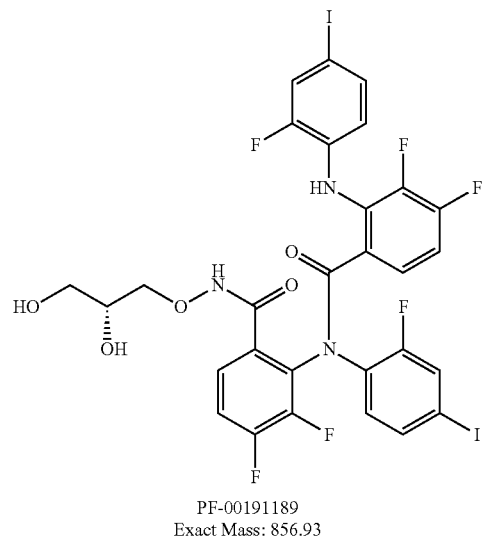 [SMILES: O=C(NOC[C@H](O)CO)c1ccc(F)c(F)c1N(C(=O)c1ccc(F)c(F)c1Nc1ccc(I)cc1F)c1ccc(I)cc1F]

PF-00191189
Exact Mass: 856.93

The crude crystallization from the final reaction mixture reduced dimeric impurity PF-00191189 to approximately 1.9% and the subsequent recrystallization further reduced it to approximately 0.4%. As a consequence, undesired polymorphs were produced. The DSC patterns indicated two different melting points ~80° C. (low melt Form II) and ~117° C. (Form I). Also during the processing, the solids crystallized at a much lower temperature than expected (actual ~10° C., expected ~40° C.). It is suspected that the unsuccessful recrystallization is due to a change in the solvent composition as a result of incomplete drying of the crude. Drying of the crude wet cake prior to ethanol dissolution was stopped after about 36 hours when the crude product was ~28 kg (26 kg theoretical).

Polymorph Transformation

Approximately 7.4 kg of PD-0325901 (mixed polymorphs) from the final EtOH/Water crystallization and precipitated materials from the earlier EtOH/Toluene filtrate were taken forward to the polymorph transformation. Both crops were separately dried in the filter until constant weights and each was dissolved in EtOH. The combined EtOH solution was analyzed by HPLC and resulted in an estimated amount of 16.4 kg PD-0325901. The recrystallization was started after removing EtOH via vacuum distillation and adjusting the solvent composition to about 5% EtOH in Toluene at 65° C. (i.e., EtOH is added dropwise at 65° C. until complete solids dissolution).

A slow 4-hour cooling ramp to 5° C. followed by 12 h stirring was performed to ensure satisfactory results. The resulting slurry was filtered and again it was completely dried in the filter until constant weight (approximately 3 days). The purified solid showed 99.8% pure PD-0325901 with not detected level of dimeric impurity PF-00191189.

The dried solid (15.4 kg) was re-dissolved in exactly 4 volumes of EtOH (62 L) off of the filter, transferred to the reactor and precipitated by a slow (~3 h) water addition (308 L) at 30-35° C., cooled to 20° C. and stirred for 12 h. The DSC analysis of a slurry sample taken at 2 h shows the solids to be completely Form IV (desired polymorph).

21.4 kg PD-0315209, 9.7 kg CDI (1.05 equiv.), 91 kg solution of 9.7% PD-0337792 in Toluene (1.1 equiv.) were used and resulted in 12.74 kg of PD-0325901 (assay 99.4%, 100% Form IV, Yield ~48%).

Example 2: Assay/Impurities and Identification of PD-0325901

PD-0325901 is separated from process impurities and degradants by reversed-phase liquid chromatography with UV detection at 275 nm. Identification of PD-0325901 is performed by obtaining either an infrared or proton NMR spectrum, in addition to the HPLC retention time. For purity evaluation, process impurities and degradants are identified by their characteristic relative retention times and quantitated by area normalization.

Chromatographic Conditions: Agilent Zorbax SB C18, 5 μm, 4.6×250 mm (or equivalent); flow rate is 1.0 mL/min; column temperature is 30° C.; detector wavelength is 275 nm; diluent is 50/50 acetonitrile/water; mobile phase A is 0.1% trifluoroacetic acid (TFA) in water; mobile phase B is methanol; and the gradient conditions below. The assay is determined against a reference standard and reported on an anhydrous, solvent free basis. Quantification of specified and unspecified impurities is reported by area percent. Total impurities is the sum of all impurities present above the reporting threshold of 0.05%.

Example 3: Single Crystal X-Ray Diffraction Analysis of Form IV

A suitable single crystal of Form IV was prepared by a method involving a different coupling agent than was used in the method disclosed in Example 1. However, the crystal yielded Form IV with the same XRPD characteristics as Form IV prepared by the method of Example 1, and was therefore of suitable purity for Form IV analysis.

The single Form IV crystal was analyzed using a Bruker D8 Venture Photon II CPAD diffractometer equipped with a CuKα INCOATEC PI4us micro-focus source (λ=1.54178 Å). The simulated PXRD pattern was calculated from the low temperature (100 K) structure and room temperature (298 K, 25° C.) unit cell parameters shown below. Unit cell at room temperature was initially determined by Difference Vectors method based on 235 reflections harvested from 151, 10 diffraction frames. Unit cell parameters were subsequently refined during data integration by Saint (Bruker (2020). SAINT. Data Reduction Software) and are based on 903 reflections recorded between 19.1 and 1.1 Å resolution. The simulated pattern was consistent with an experimental Form IV pattern as shown in FIG. 1A.

TABLE 6

Initially Determined Unit Cell Parameters at Room Temperature

| a[Å] | b[Å] | c[Å] | α[°] | β[°] | γ[°] | V[Å3] |
|---|---|---|---|---|---|---|
| 27.080(2) | 27.080(2) | 4.6971(5) | 90 | 90 | 90 | 3444.5(8) |

TABLE 7

Form IV Crystal Data and Structure Refinement

| Crystal system | Tetragonal |
|---|---|
| Space group | P4$_1$ |
| a/Å | 26.9861(4) |
| b/Å | 26.9861(4) |
| c/Å | 4.66600(10) |
| α/° | 90 |
| β/° | 90 |
| γ/° | 90 |

TABLE 7-continued

Form IV Crystal Data and Structure Refinement

| Crystal system | Tetragonal |
|---|---|
| Volume/Å$^3$ | 3398.01(12) |
| Z | 8 |
| ρcalcg/cm$^3$ | 1.885 |
| μ/mm$^{-1}$ | 15.351 |
| F(000) | 1888 |

Example 4: Capsule Formulations

Formulation Composition

| | 1 mg | | 2 mg | | 5 mg | |
|---|---|---|---|---|---|---|
| Ingredient | % (w/w) | mg/cap | % (w/w) | mg/cap | % (w/w) | mg/cap |
| Mirdametinib[a] | 0.77 | 1 | 0.77 | 2 | 5.26 | 5 |
| Microcrystalline Cellulose[b] | 93.23 | 121.2 | 93.23 | 242.4 | 89.74 | 85.25 |
| Croscarmellose sodium | 5 | 6.5 | 5 | 13 | 5 | 4.75 |
| Magnesium Stearate | 1 | 1.3 | 1 | 2.6 | 0 | 0 |
| Total | 100 | 130 | 100 | 260 | 100 | 95 |
| Capsule Shells | | Size #3 HG capsules | | Size #1 HG capsules | | Size #2 HG capsules |

HG = Hard Gelatin
[a]Based on a theoretical potency of 1.000. Actual quantity may be adjusted based on the actual potency.
[b]Quantiy of microcrystalline cellulose may be adjusted for slight potency changes of PD-0325901.

Example 5: Form IV Stability

Figure 2:
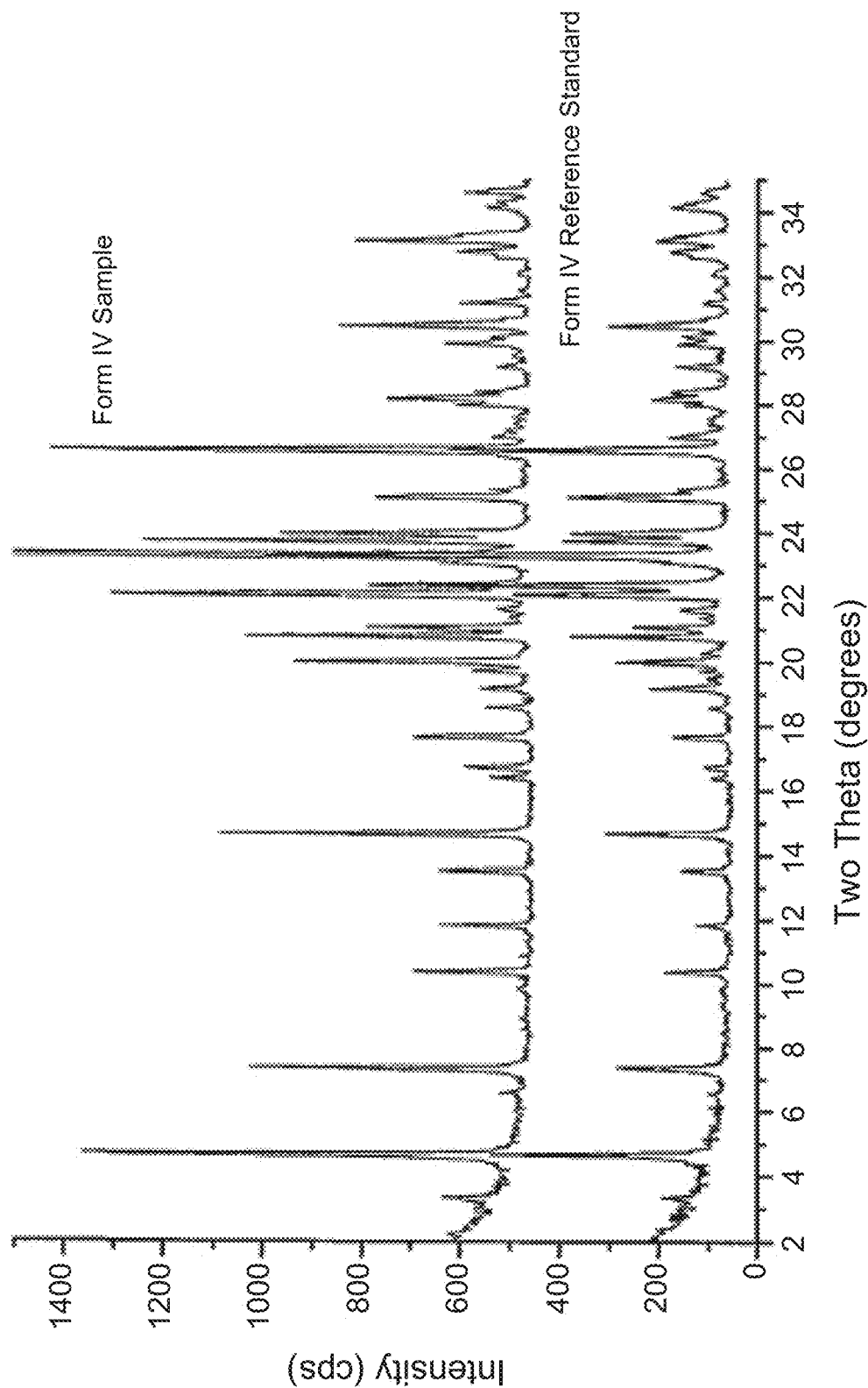
FIG. 2 is an XRPD corresponding to a batch of essentially pure Form IV of N-((R)-2,3-dihydroxypropoxy)-3,4-difluoro-2-(2-fluoro-4-iodo-phenylamino)-benzamide as initially prepared and an XRPD of a known reference standard of Form IV.
Figure 3A:
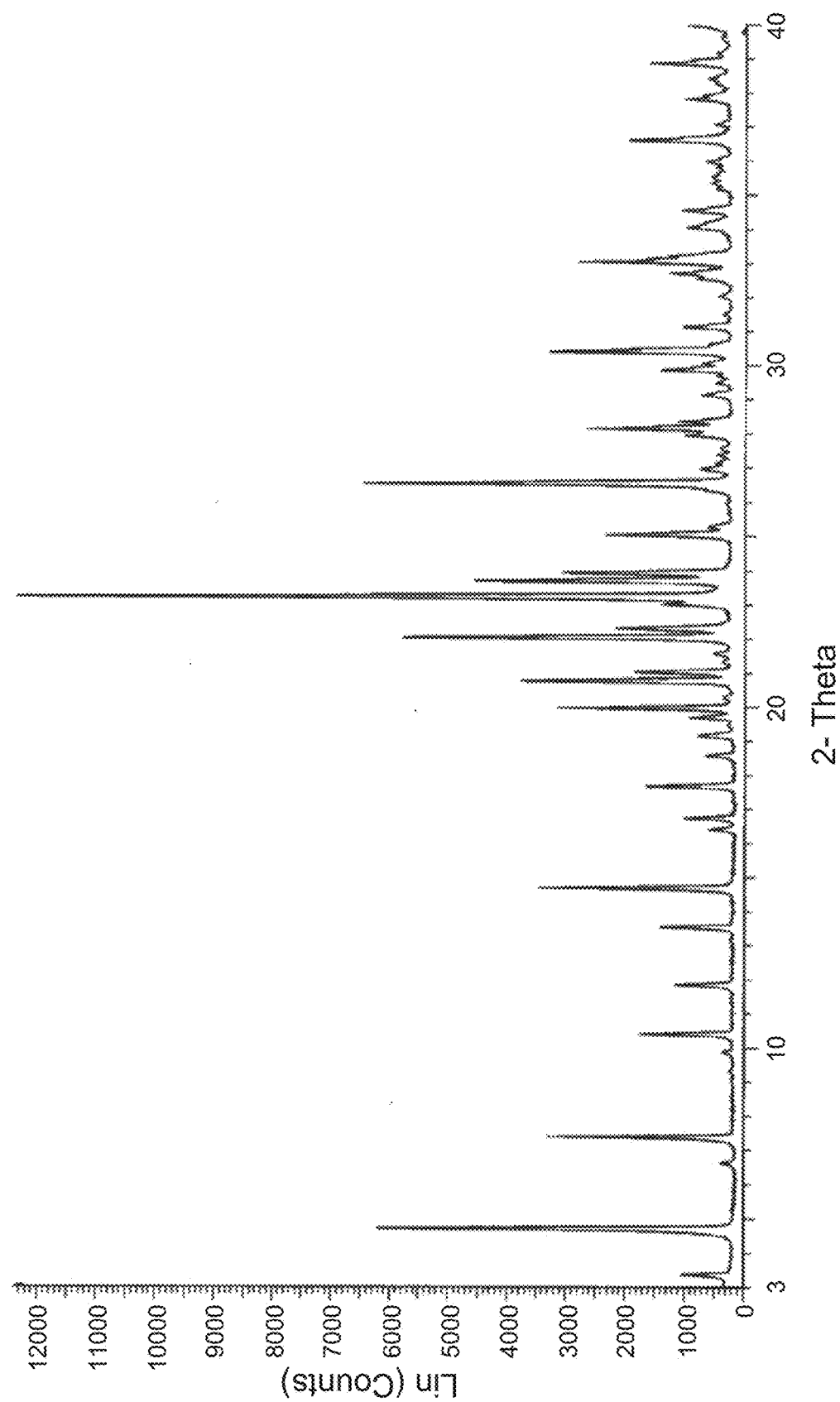
FIG. 3A is an XRPD corresponding to essentially pure Form IV of N-((R)-2,3-dihydroxypropoxy)-3,4-difluoro-2-(2-fluoro-4-iodo-phenylamino)-benzamide after storage for 68 months after production at 25° C. and 65% relative humidity.
Figure 3B:
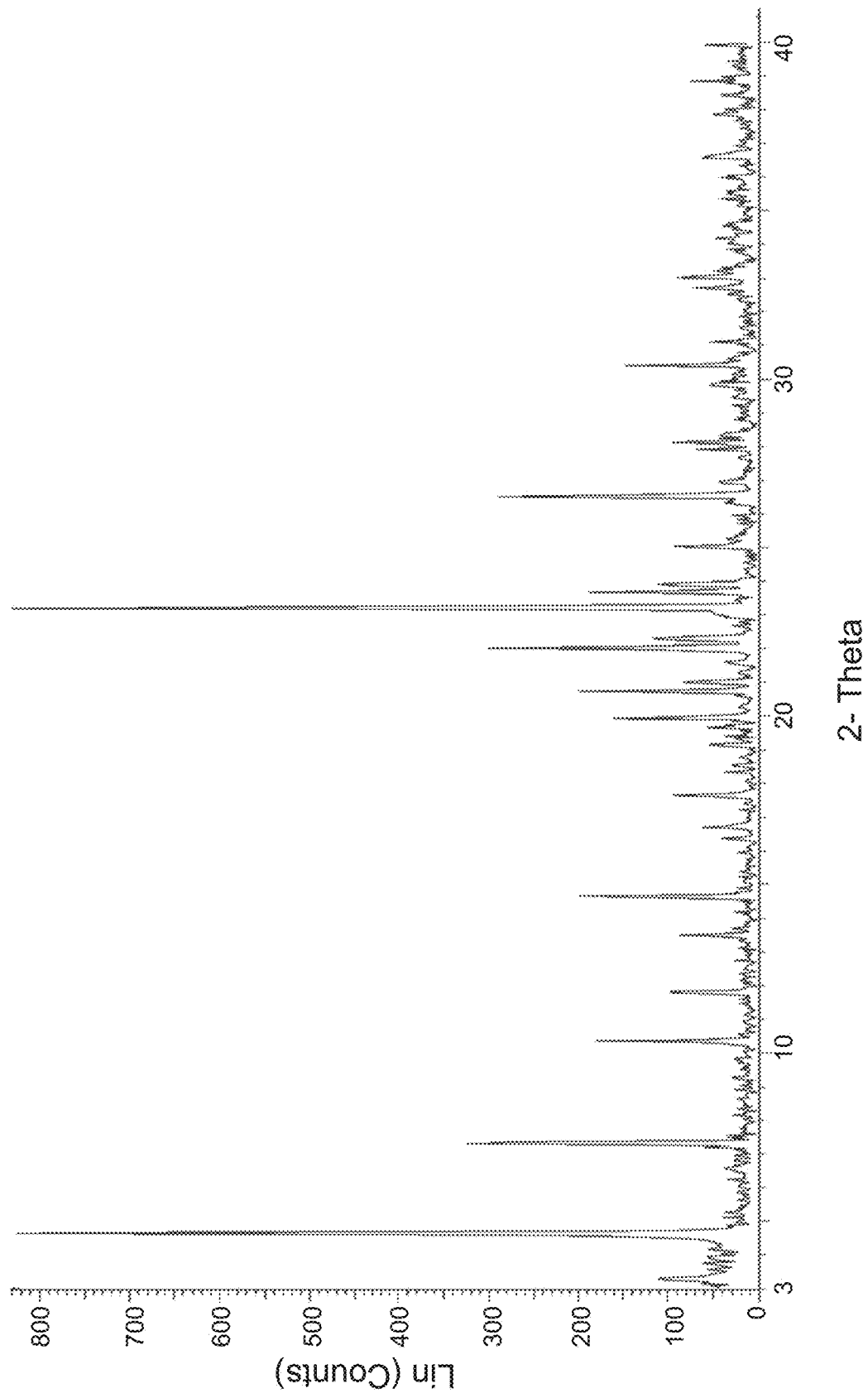
FIG. 3B is an XRPD corresponding to essentially pure Form IV of N-((R)-2,3-dihydroxypropoxy)-3,4-difluoro-2-(2-fluoro-4-iodo-phenylamino)-benzamide after storage for 140 months after production at 25° C. and 65% relative humidity.

Stability of Form IV material was determined by comparing the XRPD spectrum of a batch to a reference standard XRPD spectrum. This analysis was performed at batch release, and the XRPD spectrum obtained corresponded to that of the reference standard of Form IV (FIG. 2). The Form IV batch was then stored at 25° C. and 65% relative humidity. XRPD analysis of the stored Form IV was performed at 68 months (FIG. 3A) and again at 140 months (FIG. 31B). Undetectable changes in the XRPD spectra over time indicated stability of Form IV at 25° C. and ≤65% relative humidity.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

In addition to the various embodiments described herein, the present disclosure includes the following embodiments numbered E1 through E94. This list of embodiments is presented as an exemplary list and the application is not limited to these embodiments.

E1. A crystalline composition that is essentially pure Form IV of N-((R)-2,3-dihydroxypropoxy)-3,4-difluoro-2-(2-fluoro-4-iodo-phenylamino)-benzamide of Formula (I)

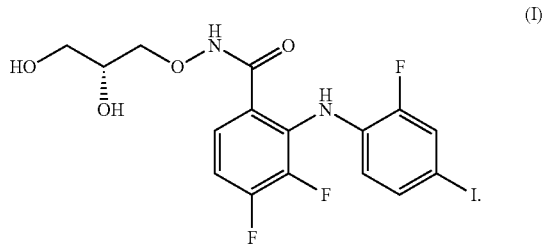 [SMILES: O=C(NOC[C@H](O)CO)c1ccc(F)c(F)c1Nc1ccc(I)cc1F]

(I)

E2. The crystalline composition of E1, wherein the crystalline composition exhibits an XRPD pattern and/or DSC profile which is substantially unchanged after storage for 3 months at standard warehouse conditions (15° C.-25° C. and ≤65% relative humidity).

E3. The crystalline composition of E1 or E2, wherein the crystalline composition exhibits an XRPD pattern and/or DSC profile which is substantially unchanged after storage for 6 months at standard warehouse conditions (15° C.-25° C. and ≤65% relative humidity).

E4. The crystalline composition of any one of E1-E3, wherein the crystalline composition exhibits an XRPD pattern and/or DSC profile which is substantially unchanged after storage for 1 year at standard warehouse conditions (15° C.-25° C. and ≤65% relative humidity).

E5. The crystalline composition of any one of E1-E4, wherein the crystalline composition exhibits an XRPD pattern and/or DSC profile which is substantially unchanged after storage for 68 months at standard warehouse conditions (15° C.-25° C. and ≤65% relative humidity).

E6. The crystalline composition of any one of E1-E5, wherein the crystalline composition exhibits an XRPD pattern and/or DSC profile which is substantially unchanged after storage for ≥140 months at standard warehouse conditions (15° C.-25° C. and S65% relative humidity).

E7. The crystalline composition of any one of E2-E6, wherein the XRPD pattern is generated using:

a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit; or a BRUKER® D8® ADVANCE™ system using Cu Kα (40 kV/40 mA) radiation and a step size of 0.03° 2θ with a LYNXEYE™ detector, configured (a) on the incidental beam side as follows: Goëbel mirror, mirror exit slit (0.2 mm), 2.5° Soller slit, beam knife, and (b) on the diffracted beam side as follows: anti-scatter slit (8 mm) and 2.5° Soller slit; and wherein samples are mounted flat on zero-background Si wafers.

E8. The crystalline composition of any one of E1-E7, wherein the DSC pattern is generated using a TA Instruments Q100 or Q2000 differential scanning calorimeter at a rate of temperature increase of about 15° C./min.

E9. The crystalline composition of any one of E1-E8, wherein the crystalline composition contains ≤0.2% of dimeric impurity PF-00191189.

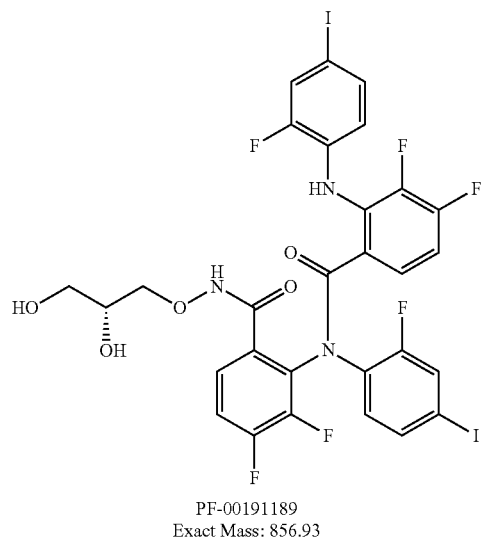 [SMILES: O=C(NOC[C@H](O)CO)c1ccc(F)c(F)c1N(C(=O)c1ccc(F)c(F)c1Nc1ccc(I)cc1F)c1ccc(I)cc1F]

PF-00191189
Exact Mass: 856.93

E10. The crystalline composition of any one of E1-E9, wherein the crystalline composition contains about 0.05% to about 0.19% by weight of dimeric impurity PF-00191189.

E11. The crystalline composition of any one of E1-E9, wherein the crystalline composition contains no detectable amount of dimeric impurity PF-00191189.

E12. A pharmaceutical composition comprising the crystalline composition of any one of E1-E11 and a pharmaceutically acceptable carrier.

E13. The pharmaceutical composition of E12, wherein the pharmaceutical composition is for oral administration.

E14. The pharmaceutical composition of E13, wherein the pharmaceutical composition is a solid dosage form.

E15. The pharmaceutical composition of any one of E12-E14, wherein the pharmaceutical composition is a tablet or capsule.

E16. The pharmaceutical composition of E15, wherein the pharmaceutical composition is a tablet.

E17. The pharmaceutical composition of E15, wherein the pharmaceutical composition is a capsule.

E18. The pharmaceutical composition of E17, wherein the capsule comprises about 1 mg of N-((R)-2,3-dihydroxypropoxy)-3,4-difluoro-2-(2-fluoro-4-iodo-phenylamino)-benzamide, wherein each component of the capsule is as follows:

a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide;

b) about 85 wt/wt % to about 95 wt/wt % of one or more diluents;

c) about 3.5 wt/wt % to about 6 wt/wt % of one or more disintegrants;

d) about 0.5 wt/wt % to about 2 wt/wt % of one or more lubricants; and e) a gelatin capsule which encapsulates components a-d.

E19. The pharmaceutical composition of E17, wherein the capsule comprises about 2 mg of N-((R)-2,3-dihydroxypropoxy)-3,4-difluoro-2-(2-fluoro-4-iodo-phenylamino)-benzamide, wherein each component of the capsule is as follows.

a) about 0.25 wt/wt % to about 1.5 wt/wt % of the crystalline composition of N-((R)-2,3-dihydroxypropoxy)-3,4-difluoro-2-(2-fluoro-4-iodo-phenylamino)-benzamide;
b) about 85 wt/wt % to about 95 wt/wt % of one or more diluents;
c) about 3.5 wt/wt % to about 6 wt/wt % of one or more disintegrants;
d) about 0.5 wt/wt % to about 2 wt/wt % of one or more lubricants; and
e) a gelatin capsule which encapsulates components a-d.

E20. The pharmaceutical composition of E17, wherein the capsule comprises about 5 mg of N-((R)-2,3-dihydroxypropoxy)-3,4-difluoro-2-(2-fluoro-4-iodo-phenylamino)-benzamide, wherein each component of the capsule is as follows:

a) about 2.5 wt/wt % to about 7.0 wt/wt % of the crystalline composition of N-((R)-2,3-dihydroxypropoxy)-3,4-difluoro-2-(2-fluoro-4-iodo-phenylamino)-benzamide;
b) about 85 wt/wt % to about 95 wt/wt % of one or more diluents;
c) about 3.5 wt/wt % to about 6 wt/wt % of one or more disintegrants; and
d) a gelatin capsule which encapsulates components a-c.

E21. The pharmaceutical composition of any one of E18-E20, wherein at least one of the diluents is selected from the group consisting of microcrystalline cellulose, lactose, mannitol, starch, and dibasic calcium phosphate.

E22. The pharmaceutical composition of E21, wherein at least one of the diluents is microcrystalline cellulose.

E23. The pharmaceutical composition of any one of E18-E22, wherein at least one of the disintegrants is selected from the group consisting of croscarmellose sodium, sodium starch glycolate, crospovidone, and alginic acid.

E24. The pharmaceutical composition of E23, wherein at least one of the disintegrants is croscarmellose sodium.

E25. The pharmaceutical composition of any one of E18-E24, wherein at least one of the lubricants is selected from the group consisting of magnesium stearate, sodium stearyl fumarate, glycerol dibehenate, and talc.

E26. The pharmaceutical composition of E25, wherein at least one of the lubricants is magnesium stearate.

E27. A method of treating a tumor, a cancer, or a Rasopathy disorder comprising administering to a subject in need of such treatment the pharmaceutical composition of any one of E12-E26.

E28. The method of E27, wherein the tumor is a neurofibroma.

E29. The method of E28, wherein the tumor is a neurofibroma associated with Neurofibromatosis Type 1.

E30. The method of any one of E27-E29, wherein the tumor is selected from the group consisting of cutaneous neurofibroma, plexiform neurofibroma, optic pathway glioma, low grade glioma, high grade glioma, or malignant peripheral nerve sheath tumor.

E31. The method of E30, wherein the tumor is plexiform neurofibroma.

E32. The method of E27, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E33. The method of E27, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E34. The method of E33, wherein the leukemia is selected from the group consisting of acute lymphocytic leukemia, acute myelogenous leukemia, chronic lymphocytic leukemia, and chronic myelogenous leukemia.

E35. The method of E33, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E36. The method of E33, wherein the lung cancer is selected from the group consisting of lung adenocarcinoma, squamous non-small cell lung cancer, non-squamous non-small cell lung cancer, and small cell lung cancer.

E37. The method of any one of E27-E36, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E38. The method of any one of E27-E37, wherein the N-((R)-2,3-dihydroxypropoxy)-3,4-difluoro-2-(2-fluoro-4-iodo-phenylamino)-benzamide is administered in a total daily dose that does not exceed 20 mg.

E39. The method of any one of E27-E37, wherein the N-((R)-2,3-dihydroxypropoxy)-3,4-difluoro-2-(2-fluoro-4-iodo-phenylamino)-benzamide is administered in a total daily dose that does not exceed 10 mg.

E40. The method of any one of E27-E37, wherein the N-((R)-2,3-dihydroxypropoxy)-3,4-difluoro-2-(2-fluoro-4-iodo-phenylamino)-benzamide is administered in a total daily dose that does not exceed 8 mg.

E41. The method of any one of E27-E37, wherein the N-((R)-2,3-dihydroxypropoxy)-3,4-difluoro-2-(2-fluoro-4-iodo-phenylamino)-benzamide is administered in a total daily dose that does not exceed 6 mg.

E42. The method of any one of E27-E41, wherein the total daily dose of the N-((R)-2,3-dihydroxypropoxy)-3,4-difluoro-2-(2-fluoro-4-iodo-phenylamino)-benzamide is administered once daily.

E43. The method of E42, wherein the total daily dose of the N-((R)-2,3-dihydroxypropoxy)-3,4-difluoro-2-(2-fluoro-4-iodo-phenylamino)-benzamide is administered once daily at a dose of about 0.1 mg to about 20 mg.

E44. The method of E42, wherein the total daily dose of the N-((R)-2,3-dihydroxypropoxy)-3,4-difluoro-2-(2-fluoro-4-iodo-phenylamino)-benzamide is administered once daily at a dose of about 2 mg.

E45. The method of E42, wherein the total daily dose of the N-((R)-2,3-dihydroxypropoxy)-3,4-difluoro-2-(2-fluoro-4-iodo-phenylamino)-benzamide is administered once daily at a dose of about 4 mg.

E46. The method of E42, wherein the total daily dose of the N-((R)-2,3-dihydroxypropoxy)-3,4-difluoro-2-(2-fluoro-4-iodo-phenylamino)-benzamide is administered once daily at a dose of about 6 mg.

E47. The method of E42, wherein the total daily dose of the N-((R)-2,3-dihydroxypropoxy)-3,4-difluoro-2-(2-fluoro-4-iodo-phenylamino)-benzamide is administered once daily at a dose of about 8 mg.

E48. The method of E42, wherein the total daily dose of the N-((R)-2,3-dihydroxypropoxy)-3,4-difluoro-2-(2-fluoro-4-iodo-phenylamino)-benzamide is administered once daily at a dose of about 20 mg.

E49. The method of any one of E27-E42, wherein the total daily dose of the N-((R)-2,3-dihydroxypropoxy)-3,4-difluoro-2-(2-fluoro-4-iodo-phenylamino)-benzamide is administered two times daily.

E50. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 0.1 mg to about 10 mg each.

E51. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 1 mg each.

E52. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 2 mg each.

E53. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 3 mg each.

E54. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 4 mg each.

E55. The method of E49, wherein the total daily dose of the N-((R)-2,3-dihydroxypropoxy)-3,4-difluoro-2-(2-fluoro-4-iodo-phenylamino)-benzamide is administered two times daily at a dose of about 10 mg each.

E56. The method of any one of E27-E55, wherein an individual dose of the N-((R)-2,3-dihydroxypropoxy)-3,4-difluoro-2-(2-fluoro-4-iodo-phenylamino)-benzamide is administered as more than one capsule or tablet.

E57. The method of any one of E27-E56, wherein the N-((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N-((R)-2,3-dihydroxypropoxy)-3,4-difluoro-2-(2-fluoro-4-iodo-phenylamino)-benzamide is administered.

E58. The method of any one of E27-E56, wherein the N-((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N-((R)-2,3-dihydroxypropoxy)-3,4-difluoro-2-(2-fluoro-4-iodo-phenylamino)-benzamide is administered.

E59. The method of any one of E27-E56, wherein the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N-((R)-2,3-dihydroxypropoxy)-3,4-difluoro-2-(2-fluoro-4-iodo-phenylamino)-benzamide; and (b) 7 days in which no N-((R)-2,3-dihydroxypropoxy)-3,4-difluoro-2-(2-fluoro-4-iodo-phenylamino)-benzamide is administered.

E60. The method of any one of E27-E56, wherein the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N-((R)-2,3-dihydroxypropoxy)-3,4-difluoro-2-(2-fluoro-4-iodo-phenylamino)-benzamide; followed by (b) 7 consecutive days in which no N-((R)-2,3-dihydroxypropoxy)-3,4-difluoro-2-(2-fluoro-4-iodo-phenylamino)-benzamide is administered.

E61. The method of any one of E57-E60, wherein the 28-day dosing cycle is repeated up to a total of 24 consecutive 28-day dosing cycles.

E62. Use of the pharmaceutical composition of any one of E12-E26 for the manufacture of a medicament for treating a tumor, a cancer, or a Rasopathy disorder.

E63. The use of any one of E62, wherein the tumor is a neurofibroma.

E64. The use of E63, wherein the tumor is a neurofibroma associated with Neurofibromatosis Type 1.

E65. The use of any one of E62-E64, wherein the tumor is selected from the group consisting of cutaneous neurofibroma, plexiform neurofibroma, optic pathway glioma, low grade glioma, high grade glioma, or malignant peripheral nerve sheath tumor.

E66. The use of E65, wherein the tumor is plexiform neurofibroma.

E67. The use of E62, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E68. The use of E62, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E69. The use of E68, wherein the leukemia is selected from the group consisting of acute lymphocytic leukemia, acute myelogenous leukemia, chronic lymphocytic leukemia, and chronic myelogenous leukemia.

E70. The use of E68, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E71. The use of E68, wherein the lung cancer is selected from the group consisting of lung adenocarcinoma, squamous non-small cell lung cancer, non-squamous non-small cell lung cancer, and small cell lung cancer.

E72. The use of any one of E62-E71, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E73. The use of any one of E62-E72, wherein the N-((R)-2,3-dihydroxypropoxy)-3,4-difluoro-2-(2-fluoro-4-iodo-phenylamino)-benzamide is administered in a total daily dose that does not exceed 20 mg.

E74. The use of any one of E62-E72, wherein the N-((R)-2,3-dihydroxypropoxy)-3,4-difluoro-2-(2-fluoro-4-iodo-phenylamino)-benzamide is administered in a total daily dose that does not exceed 10 mg.

E75. The use of any one of E62-E72, wherein the N-((R)-2,3-dihydroxypropoxy)-3,4-difluoro-2-(2-fluoro-4-iodo-phenylamino)-benzamide is administered in a total daily dose that does not exceed 8 mg.

E76. The use of any one of E62-E72, wherein the N-((R)-2,3-dihydroxypropoxy)-3,4-difluoro-2-(2-fluoro-4-iodo-phenylamino)-benzamide is administered in a total daily dose that does not exceed 6 mg.

E77. The use of any one of E62-E75, wherein the total daily dose of the N-((R)-2,3-dihydroxypropoxy)-3,4-difluoro-2-(2-fluoro-4-iodo-phenylamino)-benzamide is administered once daily.

E78. The use of E76, wherein the total daily dose of the N-((R)-2,3-dihydroxypropoxy)-3,4-difluoro-2-(2-fluoro-4-iodo-phenylamino)-benzamide is administered once daily at a dose of about 0.1 mg to about 20 mg.

E79. The use of E77, wherein the total daily dose of the N-((R)-2,3-dihydroxypropoxy)-3,4-difluoro-2-(2-fluoro-4-iodo-phenylamino)-benzamide is administered once daily at a dose of about 2 mg.

E80. The use of E77, wherein the total daily dose of the N-((R)-2,3-dihydroxypropoxy)-3,4-difluoro-2-(2-fluoro-4-iodo-phenylamino)-benzamide is administered once daily at a dose of about 4 mg.

E81. The use of E77, wherein the total daily dose of the N-((R)-2,3-dihydroxypropoxy)-3,4-difluoro-2-(2-fluoro-4-iodo-phenylamino)-benzamide is administered once daily at a dose of about 6 mg.

E82. The use of E77, wherein the total daily dose of the N-((R)-2,3-dihydroxypropoxy)-3,4-difluoro-2-(2-fluoro-4-iodo-phenylamino)-benzamide is administered once daily at a dose of about 8 mg.

E83. The use of E77, wherein the total daily dose of the N-((R)-2,3-dihydroxypropoxy)-3,4-difluoro-2-(2-fluoro-4-iodo-phenylamino)-benzamide is administered once daily at a dose of about 20 mg.

E84. The use of any one of E62-E76, wherein the total daily dose of the N-((R)-2,3-dihydroxypropoxy)-3,4-difluoro-2-(2-fluoro-4-iodo-phenylamino)-benzamide is administered two times daily.

E85. The use of E84, wherein the total daily dose of the N-((R)-2,3-dihydroxypropoxy)-3,4-difluoro-2-(2-fluoro-4-iodo-phenylamino)-benzamide is administered two times daily at a dose of about 0.1 mg to about 10 mg each.

E86. The use of E84, wherein the total daily dose of the N-((R)-2,3-dihydroxypropoxy)-3,4-difluoro-2-(2-fluoro-4-iodo-phenylamino)-benzamide is administered two times daily at a dose of about 1 mg each.

E87. The use of E84, wherein the total daily dose of the N-((R)-2,3-dihydroxypropoxy)-3,4-difluoro-2-(2-fluoro-4-iodo-phenylamino)-benzamide is administered two times daily at a dose of about 2 mg each.

E88. The use of E84, wherein the total daily dose of the N-((R)-2,3-dihydroxypropoxy)-3,4-difluoro-2-(2-fluoro-4-iodo-phenylamino)-benzamide is administered two times daily at a dose of about 3 mg each.

E89. The use of E84, wherein the total daily dose of the N-((R)-2,3-dihydroxypropoxy)-3,4-difluoro-2-(2-fluoro-4-iodo-phenylamino)-benzamide is administered two times daily at a dose of about 4 mg each.

E90. The use of E76, wherein the total daily dose of the N-((R)-2,3-dihydroxypropoxy)-3,4-difluoro-2-(2-fluoro-4-iodo-phenylamino)-benzamide is administered two times daily at a dose of about 10 mg each.

E91. The use of any one of E61-E90, wherein an individual dose of the N-((R)-2,3-dihydroxypropoxy)-3,4-difluoro-2-(2-fluoro-4-iodo-phenylamino)-benzamide is administered as more than one capsule or tablet.

E92. The use of any one of E62-E91, wherein the N-((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N-((R)-2,3-dihydroxypropoxy)-3,4-difluoro-2-(2-fluoro-4-iodo-phenylamino)-benzamide is administered.

E93. The use of any one of E62-E91, wherein the N-((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N-((R)-2,3-dihydroxypropoxy)-3,4-difluoro-2-(2-fluoro-4-iodo-phenylamino)-benzamide is administered.

E94. The use of any one of E62-E91, wherein the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N-((R)-2,3-dihydroxypropoxy)-3,4-difluoro-2-(2-fluoro-4-iodo-phenylamino)-benzamide; and (b) 7 days in which no N-((R)-2,3-dihydroxypropoxy)-3,4-difluoro-2-(2-fluoro-4-iodo-phenylamino)-benzamide is administered.

E95. The use of any one of E62-E91, wherein the N-((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N-((R)-2,3-dihydroxypropoxy)-3,4-difluoro-2-(2-fluoro-4-iodo-phenylamino)-benzamide; followed by (b) 7 consecutive days in which no N-((R)-2,3-dihydroxypropoxy)-3,4-difluoro-2-(2-fluoro-4-iodo-phenylamino)-benzamide is administered.

E96. The use of any one of E92-E95, wherein the 28-day dosing cycle is repeated up to a total of 24 consecutive 28-day dosing cycles.

What is claimed is:

1. A method of treating Neurofibromatosis in a patient in need thereof comprising administering a pharmaceutical composition comprising 1 mg to 4 mg N-((R)-2,3-dihydroxypropoxy)-3,4-difluoro-2-(2-fluoro-4-iodo-phenylamino)-benzamide Form IV characterized by an XRPD pattern having peaks at 4.6±0.2, 13.5±0.2 and 16.7±0.2 degrees two theta.

2. The method of claim 1 wherein the pharmaceutical composition comprises 1 mg N-((R)-2,3-dihydroxypropoxy)-3,4-difluoro-2-(2-fluoro-4-iodo-phenylamino)-benzamide.

3. The method of claim 1 wherein the pharmaceutical composition comprises 2 mg N-((R)-2,3-dihydroxypropoxy)-3,4-difluoro-2-(2-fluoro-4-iodo-phenylamino)-benzamide.

4. The method of claim 1 wherein the pharmaceutical composition comprises 3 mg N-((R)-2,3-dihydroxypropoxy)-3,4-difluoro-2-(2-fluoro-4-iodo-phenylamino)-benzamide.

5. The method of claim 1 wherein the pharmaceutical composition comprises 4 mg N-((R)-2,3-dihydroxypropoxy)-3,4-difluoro-2-(2-fluoro-4-iodo-phenylamino)-benzamide.

6. A method of treating Neurofibromatosis in a patient in need thereof comprising administering a pharmaceutical composition comprising 1 mg to 4 mg N-((R)-2,3-dihydroxypropoxy)-3,4-difluoro-2-(2-fluoro-4-iodo-phenylamino)-benzamide Form IV characterized by an XRPD pattern substantially as shown in FIG. 1A.

* * * * *